US005545549A

United States Patent [19]

Gerald et al.

[11] Patent Number: 5,545,549

[45] Date of Patent: Aug. 13, 1996

[54] DNA ENCODING A HUMAN NEUROPEPTIDE Y/PEPTIDE YY (Y2) RECEPTOR AND USES THEREOF

[75] Inventors: Christophe Gerald, Ridgewood; Mary W. Walker, Elmwood Park; Theresa Branchek, Teaneck, all of N.J.; Richard L. Weinshank, New York, N.Y.

[73] Assignee: Synaptic Pharmaceutical Corporation, Paramus, N.J.

[21] Appl. No.: 192,288

[22] Filed: Feb. 3, 1994

[51] Int. Cl.$^6$ .............................. C07H 21/04; C12N 5/10; C12N 15/12; C12N 15/63

[52] U.S. Cl. .................... 435/240.2; 435/69.1; 435/70.3; 435/71.2; 435/320.1; 536/23.1; 536/23.5

[58] Field of Search ................................ 536/23.1, 23.5, 536/24.31; 435/69.1, 70.1, 70.3, 71.1, 71.2, 172.1, 240.1, 240.2, 320.1

[56] References Cited

PUBLICATIONS

Wahlestedt, C., et al. Neuropeptide Y Receptor Subtypes, Y1 and Y2. Ann. N. Y. Acad. Sci. 1990; 611:7–26 (Exhibit B).

Wahlestedt, C., et al. Indentification of Cultured Cells Selectively Expressing Y1–, Y2–, Or Y3–Type Receptors for Neuropeptide Y/Peptide YY. Life Sciences 1991; 50(4): PL–7 –PL–12 (Exhibit C).

Sheikh, S. P., et al. Binding of Monoiodinated Neuropeptide Y to Hippocampal Membranes and Human Neuroblastoma Cell Lines. J. Biol. Chem. 1989; 264(12):6648–6654 (Exhibit D).

Larhammar, D., et al. Cloning and Functional Expression of a Human Neuropeptide Y/Peptide YY Receptor of the Y1 Type. J. Biol. Chem. 1992; 267(16):10935–10938 (Exhibit E).

Wahlestedt et al Life Sciences 50 PL–7 –PL–12 (1991)

Kluxen et al PNAS 89 4618–4622 (1992).

Sasaki et al Nature 351 230–233 (1991).

Wallace et al Method in Ehzym–152 432–442 (1987).

Inui et al Ann. N.Y. Acad Sci. 611 350–14 352 (1990).

Narray et al.Neurosci. Lett. 140 273–276 (1992).

Blasquez et al Brocin Res. 596 163–168 (1992).

Brcin Res. 596 163–168 (1992).

Xie et al. PNAS 89 4124–4128 (1992).

Sasaki et al. Nature 351 230–233 (1991) Wallace et al. Method in Euzym–152 432–442 (1987).

Inui et al. Ann. N. Y. Acad Sci. 611 350–352 (1990) Narray et al. Neurosci. Lett. 140 273–276 (1992).

Blasquez et al. Brniu Res. 596 163–168 (1992) Xie et al. PNAS 89 4124–4128 (1992).

*Primary Examiner*—Stephen G. Walsh
*Assistant Examiner*—Stephen Gucker
*Attorney, Agent, or Firm*—John P. White

[57] ABSTRACT

This invention provides an isolated nucleic acid molecule encoding a human Y2 receptor, an isolated protein which is a human Y2 receptor, vectors comprising an isolated nucleic acid molecule encoding a human Y2 receptors, mammalian cells comprising such vectors, antibodies directed to the human Y2 receptor, nucleic acid probes useful for detecting nucleic acid encoding human Y2 receptors, antisense oligonucleotides complementary to any sequences of a nucleic acid molecule which encodes a human Y2 receptor, pharmaceutical compounds related to human Y2 receptors, and nonhuman transgenic animals which express DNA a normal or a mutant human Y2 receptor. This invention further provides methods for determining ligand binding, detecting expression, drug screening, and treatment involving the human Y2 receptor.

16 Claims, 11 Drawing Sheets

FIGURE 1

1 GACTCTTGTGCTGGTTGCAGGCCAAGTGGACCTGTACTGAAAATGGGTCCAATAGGTGCA 60
61 GAGGCTGATGAGAACCAGACAGTGGAAGAAATGAAGGTGGAACAATACGGGCCACAAACA 120
121 ACTCCTAGAGGTGAACTGGTCCCTGACCCTGAGCCAGAGCTTATAGATAGTACCAAGCTG 180
181 ATTGAGGTACAAGTTGTTCTCATATTGGCCTACTGCTCCATCATCTTGCTTGGGGTAATT 240
241 GGCAACTCCTTGGTGATCCATGTGGTGATCAAATTCAAGAGCATGCGCACAGTAACCAAC 300
301 TTTTTCATTGCCAATCTGGCTGTGGCAGATCTTTTGGTGAACACTCTGTGTCTACCGTTC 360
361 ACTCTTACCTATACCTTAATGGGGGAGTGGAAAATGGGTCCTGTCCTGTGCCACCTGGTG 420
421 CCCTATGCCCAGGGCCTGGCAGTACAAGTATCCACAATCACCTTGACAGTAATTGCCCTG 480
481 GACCGGCACAGGTGCATCGTCTACCACCTAGAGAGCAAGATCTCCAAGCGAATCAGCTTC 540
541 CTGATTATTGGCTTGGCCTGGGGCATCAGTGCCCTGCTGGCAAGTCCCCTGGCCATCTTC 600
601 CGGGAGTATTCGCTGATTGAGATCATCCCGGACTTTGAGATTGTGGCCTGTACTGAAAAG 660
661 TGGCCTGGCGAGGAGAAGAGCATCTATGGCACTGTCTATAGTCTTTCTTCCTTGTTGATC 720
721 TTGTATGTTTTGCCTCTGGGCATTATATCATTTTCCTACACTCGCATTTGGAGTAAATTG 780
781 AAGAACCATGTCAGTCCTGGAGCTGCAAATGACCACTACCATCAGCGAAGGCAAAAAACC 840
841 ACCAAAATGCTGGTGTGTGTGGTGGTGGTGTTTGCGGTCAGCTGGCTGCCTCTCCATGCC 900
901 TTCCAGCTTGCCGTTGACATTGACAGCCAGGTCCTGGACCTGAAGGAGTACAAACTCATC 960
961 TTCACAGTGTTCCACATCATCGCCATGTGCTCCACTTTTGCCAATCCCCTTCTCTATGGC 1020
1021 TGGATGAACAGCAACTACAGAAAGGCTTTCCTCTCGGCCTTCCGCTGTGAGCAGCGGTTG 1080
1081 GATGCCATTCACTCTGAGGTGTCCGTGACATTCAAGGCTAAAAAGAACCTGGAGGTCAGA 1140
1141 AAGAACAGTGGCCCCAATGACTCTTTCACAGAGGCTACCAATGTCTAAGGAAGCTGTGGT 1200
1201 GTGAAAATGTATGGATGAATTCTGACCAGAGCTATGAATCTGGTTGATGGCGGCTCACAA 1260
1261 GTGAAAACTGATTTCCCATT 1280

FIGURE 2

| | | | | | | | | | | | | | | | | | | | | | |
|---|---|---|---|---|---|---|---|---|---|---|---|---|---|---|---|---|---|---|---|---|---|
| | | | | | | | | | | | | | | | M | G | P | I | G | A | 6 |
| 7 | E | A | D | E | N | Q | T | V | E | E | M | K | V | E | Q | Y | G | P | Q | T | 26 |
| 27 | T | P | R | G | E | L | V | P | D | P | E | P | E | L | I | D | S | T | K | L | 46 |
| 47 | T | L | T | Y | T | L | M | G | E | W | K | M | G | P | V | L | C | H | L | V | 66 |
| 67 | G | N | S | L | V | I | H | V | V | I | K | F | K | S | M | R | T | V | T | N | 86 |
| 87 | I | E | V | Q | V | V | L | I | L | A | Y | C | S | I | I | L | L | G | V | I | 106 |
| 107 | F | F | I | A | N | L | A | V | A | D | L | L | V | N | T | L | C | L | P | F | 126 |
| 127 | P | Y | A | Q | G | L | A | V | Q | V | S | T | I | T | L | T | V | I | A | L | 146 |
| 147 | D | R | H | R | C | I | V | Y | H | L | E | S | K | I | S | K | R | I | S | F | 166 |
| 167 | L | I | I | G | L | A | W | G | I | S | A | L | L | A | S | P | L | A | I | F | 186 |
| 187 | R | E | Y | S | L | I | E | I | I | P | D | F | E | I | V | A | C | T | E | K | 206 |
| 207 | W | P | G | E | E | K | S | I | Y | G | T | V | Y | S | L | S | S | L | L | I | 226 |
| 227 | L | Y | V | L | P | L | G | I | I | S | F | S | Y | T | R | I | W | S | K | L | 246 |
| 247 | K | N | H | V | S | P | G | A | A | N | D | H | Y | H | Q | R | R | Q | K | T | 266 |
| 267 | T | K | M | L | V | C | V | V | V | V | F | A | V | S | W | L | P | L | H | A | 286 |
| 287 | F | Q | L | A | V | D | I | D | S | Q | V | L | D | L | K | E | Y | K | L | I | 306 |
| 307 | F | T | V | F | H | I | I | A | M | C | S | T | F | A | N | P | L | L | Y | G | 326 |
| 327 | W | M | N | S | N | Y | R | K | A | F | L | S | A | F | R | C | E | Q | R | L | 346 |
| 347 | D | A | I | H | S | E | V | S | V | T | F | K | A | K | K | N | L | E | V | R | 366 |
| 367 | K | N | S | G | P | N | D | S | F | T | E | A | T | N | V | * | | | | | 381 |

| FIGURE 3A |
|---|
| FIGURE 3B |
| FIGURE 3C |
| FIGURE 3D |

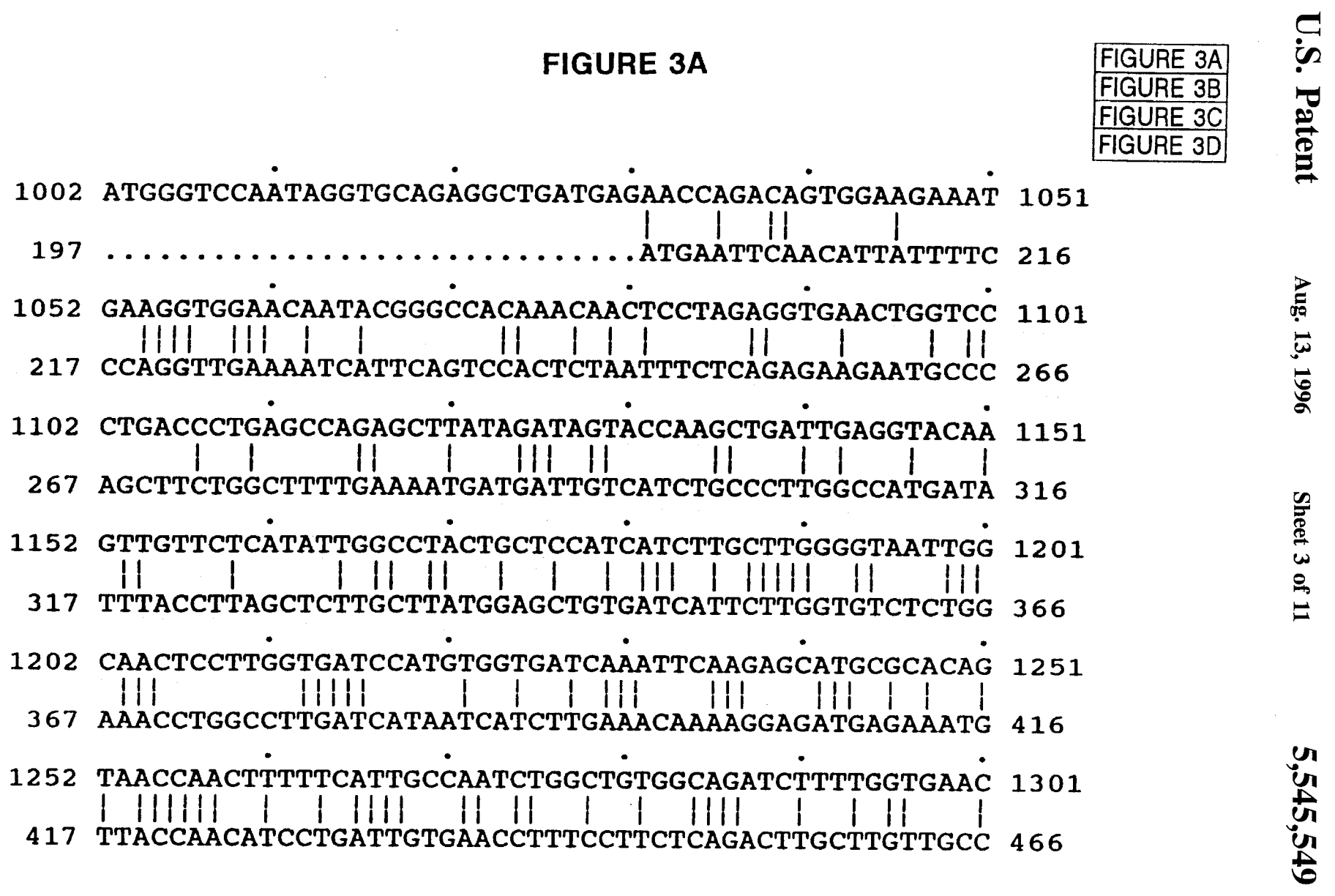

FIGURE 3A

```
1002 ATGGGTCCAATAGGTGCAGAGGCTGATGAGAACCAGACAGTGGAAGAAAT 1051
 197 ..............................ATGAATTCAACATTATTTTC 216

1052 GAAGGTGGAACAATACGGGCCACAAACAACTCCTAGAGGTGAACTGGTCC 1101
 217 CCAGGTTGAAAATCATTCAGTCCACTCTAATTTCTCAGAGAAGAATGCCC 266

1102 CTGACCCTGAGCCAGAGCTTATAGATAGTACCAAGCTGATTGAGGTACAA 1151
 267 AGCTTCTGGCTTTTGAAAATGATGATTGTCATCTGCCCTTGGCCATGATA 316

1152 GTTGTTCTCATATTGGCCTACTGCTCCATCATCTTGCTTGGGGTAATTGG 1201
 317 TTTACCTTAGCTCTTGCTTATGGAGCTGTGATCATTCTTGGTGTCTCTGG 366

1202 CAACTCCTTGGTGATCCATGTGGTGATCAAATTCAAGAGCATGCGCACAG 1251
 367 AAACCTGGCCTTGATCATAATCATCTTGAAACAAAAGGAGATGAGAAATG 416

1252 TAACCAACTTTTTCATTGCCAATCTGGCTGTGGCAGATCTTTTGGTGAAC 1301
 417 TTACCAACATCCTGATTGTGAACCTTTCCTTCTCAGACTTGCTTGTTGCC 466
```

FIGURE 3B

```
              .         .         .         .         .
1302 ACTCTGTGTCTACCGTTCACTCTTACCTATACCTTAATGGGGGAGTGGAA 1351
     |   ||||||| || || ||  ||  ||| || |||||||   | |||
 467 ATCATGTGTCTCCCCTTTACATTTGTCTACACATTAATGGACCACTGGGT 516
              .         .         .         .         .
1352 AATGGGTCCTGTCCTGTGCCACCTGGTGCCCTATGCCCAGGGCCTGGCAG 1401
       | |||   |   ||||  |  ||   || | ||  ||  |  |  ||
 517 CTTTGGTGAGGCGATGTGTAAGTTGAATCCTTTTGTGCAATGTGTTTCAA 566
              .         .         .         .         .
1402 TACAAGTATCCACAATCACCTTGACAGTAATTGCCCTGGACCGGCACAGG 1451
     |    || ||||   || |  ||    | |||||  |||| || ||   |
 567 TCACTGTGTCCATTTTCTCTCTGGTTCTCATTGCTGTGGAACGACATCAG 616
              .         .         .         .         .
1452 TGCATCGTCTACCACCTAGAGAGCAAGATCTCCAAGCGAATCAGCTTCCT 1501
        ||  || |||  | || | | |        ||  ||      |   |
 617 CTGATAATCAACCCTCGAGGGTGGAGACCAAATAATAGACATGCTTATGT 666
              .         .         .         .         .
1502 GATTATTGGCTTGGCCTGGGGCATCAGTGCCCTGCTGGCAAGTCCCCTGG 1551
        |||||   ||   |||| | |   ||    |||      |  |||
 667 AGGTATTGCTGTGATTTGGGTCCTTGCTG..TGGCTTCTTCTTTGCCTTT 714
              .         .         .         .         .
1552 CCATCTTCCGGGAGTATTCGCTGATTGAGATCATCCCGGACTTTGAGATT 1601
     ||   |      |||| |  |||| ||||    |||   |  |     ||
 715 CCTGATCTACCAAGTAATGACTGA.TGAGCCGTTCCAAAATGTAACACTT 763
```

FIGURE 3C

```
1602 GTGGCCTGTACTGAAAAGTGGCCTGGCGAGGAGAA.........GAGCAT 1642
 764 GATGCGTACAAAGACAAATACGTGTGCTTTGATCAATTTCCATCGGACTC 813

1643 CTATGGCACTGTCTATAGTCTTTCTTCCTTGTTGATCTTGTATGTTTTGC 1692
 814 TCATAGGTTGTCTTATACCACTCTCCTCTTGGTGCTGCAGTATTTTGGTC 863

1693 CTCTGGGCATTATATCATTTTCCTACACTCGCATTT........GGAGTA 1734
 864 CACTTTGTTTTATATTTATTTGCTACTTCAAGATATATATACGCCTAAAA 913

1735 AATTGAAGAACCATGTCAGTCCTGGAGCTGCAAATGACCACTACCATCAG 1784
 914 AGGAGAAACAACATGATGGACAAGATGAGAGACAATAAGTACAGGTCCAG 963

1785 CGAAGGCAAAA.AACCACCAAAATGCTGGTGTGTGGTGGTGGTGTTTG 1833
 964 TGAAACCAAAAGAATCAATATCATGCTGCTCTCCATTGTGGTAGCATTTG 1013

1834 CGGTCAGCTGGCTGCCTCTCCATGCCTTCCAGCTTGCCGTTGACATTGAC 1883
1014 CAGTCTGCTGGCTCCCTCTTACCATCTTTAACACTGTGTTTGATTGGAAT 1063
```

FIGURE 3D

```
                  .         .         .         .         .
1884 AGCCAGGTCCTGGACCTGAAGGAGTACAAACTCATCTTCACAGTGTTCCA 1933
        ||| || | |         |  |||| ||  | |||    | | |||
1064 CATCAGATCATTGCTACCTGCAACCACAATCTGTTATTCCTGCTCTGCCA 1113
                  .         .         .         .         .
1934 CATCATCGCCATGTGCTCCACTTTTGCCAATCCCCTTCTCTATGGCTGGA 1983
     | |||  || |||   ||||||| || ||| ||| |  | ||||| |
1114 CCTCACAGCAATGATATCCACTTGTGTCAACCCCATATTTTATGGGTTCC 1163
                  .         .         .         .         .
1984 TGAACAGCAACTACAGAAAGGCTTTCCTCTCGGCCTTCCGC...TGTGAG 2030
     ||||||  |||| |   |  |  || |  |    ||||  |   |||||
1164 TGAACAAAAACTTCCAGAGAGACTTGCAGTTCTTCTTCAACTTTTGTGAT 1213
                  .         .         .         .         .
2031 CAGCGGTTGGATGCCATTCACTCTGAGGTGTCCGTGACATTCAAG..... 2075
        ||||     |    | | | |||       |  |  | || |
1214 TTCCGGTCTCGGGATGATGATTATGAAACAATAGCCATGTCCACGATGCA 1263
                  .         .         .         .         .
2076 .........GCTAAAAAGAACCTGGAGGTCAGAAAGAACAGTGGC.CCCA 2115
                  ||||   | | || |  || |||  |||| ||    |
1264 CACAGATGTTTCCAAAACTTCTTTGAAGCAAGCAAGCCCAGTCGCATTTA 1313
                  .         .         .
2116 ATGACTCTTTCACAGAGGCTACCAATGTCTAA...... 2147
     |  |      ||   | | |   ||||   ||
1314 AAAAAATCAACAACAATGATGATAATGAAAAAATCTGA 1351
```

FIGURE 4A

| FIGURE 4A |
|---|
| FIGURE 4B |

```
  1 MGPIGAEADENQTVEEMKVEQYGPQTTPRGELVPDPEPELIDSTKLIEVQ  50
    |...  .. ||:.|.     ..::.......  .:  |         |:   :.:
  1 MNSTLFSQVENHSVH....SNFSEKNAQLLAFEND......DCHLPLAMI  40

 51 VVLILAYCSIILLGVIGNSLVIHVVIKFKSMRTVTNFFIANLAVADLLVN 100
    ..| |||..:|:|||  ||   :|  :::| |.||.|||::|.||...||||.
 41 FTLALAYGAVIILGVSGNLALIIIILKQKEMRNVTNILIVNLSFSDLLVA  90

101 TLCLPFTLTYTLMGEWKMGPVLCHLVPYAQGLAVQVSTITLTVIALDRHR 150
    .:|||||:.||||:.|   :|..:|.|  |:.|.:.:  ||.:.|.:||::||.
 91 IMCLPFTFVYTLMDHWVFGEAMCKLNPFVQCVSITVSIFSLVLIAVERHQ 140

151 CIVYHLESKISKRISFLIIGLAWGISALLASPLAIFREYSLIEIIPDFEI 200
     |:  . :.: ..| .:: |:: |.:..  . |: |:.  .  |  :.:..:
141 LIINPRGWRPNNRHAYVGIAVIWVLAVASSLPFLIYQVMT.DEPFQNVTL 189
```

FIGURE 4B

```
             .         .         .         .         .
201 VACTEKW......PGEEKSIYGTVVYSLSSLLILYVLPLGIISFSYTRIW 243
     |:.:|:       .:..:  |.|:.    |:: |. ||.:| ::| :|:
190 DAYKDKYVCFDQFPSDSHRLSYTTLL....LVLQYFGPLCFIFICYFKIY 235

             .         .         .         .         .
244 SKLK..NHVSPGAANDHYHQRRQKTTK.MLVCVVVVFAVSWLPLHAFQLA 290
     :||  |:: .   ::.|: .  |  .. ||:::||.|||:||||  |. .
236 IRLKRRNNMMDKMRDNKYRSSETKRINIMLLSIVVAFAVCWLPLTIFNTV 285

             .         .         .         .         .
291 VDIDSQVLDLKEYKLIFTVFHIIAMCSTFANPLLYGWMNSNYRKAF.... 336
    .| : |::.  :..|:| : |:.||.|| .||::||::|.|:.:.:
286 FDWNHQIIATCNHNLLFLLCHLTAMISTCVNPIFYGFLNKNFQRDLQFFF 335

             .         .         .         .         .
337 .LSAFRCEQR......LDAIHSEVSVT.FKAKKNLEVRK..NSGPNDSFT 376
     ::.||: :       :..:|.:|| | :|. . :..:|  |.:.|:.:
336 NFCDFRSRDDDYETIAMSTMHTDVSKTSLKQASPVAFKKINNNDDNEKI* 385

377 EATNV*                                             381
```

DNA ENCODING A HUMAN NEUROPEPTIDE Y/PEPTIDE YY (Y2) RECEPTOR AND USES THEREOF

BACKGROUND OF THE INVENTION

Throughout this application, various publications are referenced in parenthesis by number. Full citations for these references may be found at the end of the specification immediately preceding the claims. The disclosure of these publications is hereby incorporated by reference into this application to describe more fully the art to which this invention pertains.

Neuropeptides are small peptides originating from large precursor proteins synthesized by peptidergic neurons and endocrine/paracrine cells. They hold promise for treatment of neurological, psychiatric, and endocrine disorders (46). Often the precursors contain multiple biologically active peptides. There is great diversity of neuropeptides in the brain caused by alternative splicing of primary gene transcripts and differential precursor processing. The neuropeptide receptors serve to discriminate between ligands and to activate the appropriate signals. Thus, it is expected that the receptors for neuropeptides consist of a large number of members.

Neuropeptide Y (NPY), a 36-amino acid peptide, is the most abundant neuropeptide to be identified in mammalian brain. NPY is an important regulator in both the central and peripheral nervous systems (47) and influences a diverse range of physiological parameters, including effects on psychomotor activity, food intake, central endocrine secretion, and vasoactivity in the cardiovascular system. High concentrations of NPY are found in the sympathetic nerves supplying the coronary, cerebral, and renal vasculature and have contributed to vasoconstriction. NPY binding sites have been identified in a variety of tissues, including spleen (48), intestinal membranes, brain (49), aortic smooth muscle (50), kidney, testis, and placenta (2). In addition, binding sites have been reported in a number of rat and human cell lines (eg. Y1 in SK-N-MC, MC-IXC, CHP-212, and PC12 cells; Y2 in SK-N-Be(2), CHP-234, and SMS-MSN) (51,5).

Neuropeptide Y (NPY) receptor pharmacology is currently defined by structure activity relationships within the pancreatic polypeptide family (1, 2). This family includes NPY, which is synthesized primarily in neurons; peptide YY (PYY), which is synthesized primarily by endocrine cells in the gut; and pancreatic polypeptide (PP), which is synthesized primarily by endocrine cells in the pancreas. These 36 amino acid peptides have a compact helical structure involving a "PP-fold" in the middle of the peptide. Specific features include a polyproline helix in residues 1 through 8, a β-turn in residues 9 through 14, an α-helix in residues 15 through 30, an outward-projecting C-terminus in residues 30 through 36, and a carboxy terminal amide which appears to be critical for biological activity (3). The peptides have been used to define at least four receptor subtypes known as Y1, Y2, Y3, and PP. Y1 receptor recognition by NPY involves both N- and C-terminal regions of the peptide; exchange of $Gln^{34}$ with $Pro^{34}$ is fairly well tolerated (3, 4, 5). Y2 receptor recognition by NPY depends primarily upon the four C-terminal residues of the peptide ($Arg^{33}$-$Gln^{34}$-$Arg^{35}$-$Tyr^{36}$-$NH_2$) preceded by an amphipathic α-helix (3, 6, 7); exchange of $Gln^{34}$ with $Pro^{34}$ is not well tolerated (4, 5). Y3 receptor recognition is characterized by a strong preference for NPY over PYY (8). Exchange of $Gln^{34}$ in NPY with $Pro^{34}$ is reasonably well tolerated by the Y3 receptor but PP, which also contains $Pro^{34}$, does not bind well (8). The PP receptor is reported to bind tightly to PP, less so to [$Leu^{31}$, $Pro^{34}$]NPY, and even less so to NPY (3, 9). The only NPY receptor which has been cloned to date is the Y1 receptor gene, from mouse (12), rat (52), and human (10). One of the key pharmacological features which distinguish Y1 and Y2 is the fact that the Y1 receptor (and not the Y2 receptor) responds to an analog of NPY modified at residues 31 and 34 ([$Leu^{31}$,$Pro^{34}$]NPY), whereas the Y2 receptor (and not the Y1 receptor) has high affinity for the NPY peptide carboxyl-terminal fragment NPY-(13–36) (53,4).

Receptor genes for the other two structurally related peptides, peptide YY (PYY) and pancreatic polypeptide (PP), also have not been cloned. Peptide YY occurs mainly in endocrine cells in the lower gastrointestinal tract (54). Receptors for PYY were first described in the rat small intestine (55). This receptor has been defined as PYY-preferring because it displays a 5–10 fold higher affinity for PYY than for NPY (55,56). Recently, a cell line, PKSV-PCT, derived from the proximal tubules of kidneys, has been described to express receptors for PYY (57).

In the last two years, following unsuccessful attempts to clone the Y2 receptor based on homology cloning strategies, only the rat and human Y1 cDNAs have been cloned (10, 11). This success was based on identifying the randomly cloned FC5 "orphan receptor" (12). We now report the isolation by expression cloning of a human hippocampal Y2 cDNA clone and its full pharmacological characterization.

SUMMARY OF THE INVENTION

This invention provides an isolated nucleic acid molecule encoding a human Y2 receptor.

This invention also provides an isolated protein which is a human Y2 receptor.

This invention provides a vector comprising an isolated nucleic acid molecule encoding a human Y2 receptor.

This invention also provides vectors such as plasmids comprising a DNA molecule encoding a human Y2 receptor, adapted for expression in a bacterial cell, a yeast cell, an insect cell or a mammalian cell which additionally comprise the regulatory elements necessary for expression of the DNA in the bacterial, yeast, insect or mammalian cells operatively linked to the DNA encoding the Y2 receptor as to permit expression thereof.

This invention provides a mammalian cell comprising a DNA molecule encoding a human Y2 receptor.

This invention provides a nucleic acid probe comprising a nucleic acid molecule of at least 15 nucleotides capable of specifically hybridizing with a unique sequence included within the sequence of a nucleic acid molecule encoding a human Y2 receptor.

This invention provides an antisense oligonucleotide having a sequence capable of specifically hybridizing with any sequences of an mRNA molecule which encodes a human Y2 receptor so as to prevent translation of the mRNA molecule.

This invention provides an antibody directed to a human Y2 receptor.

This invention provides a transgenic nonhuman mammal expressing DNA encoding a human Y2 receptor. This invention further provides a transgenic nonhuman mammal whose genome comprises antisense DNA complementary to DNA encoding a human Y2 receptor so placed as to be transcribed into antisense mRNA which is complementary to mRNA encoding a Y2 receptor and which hybridizes to mRNA encoding a Y2 receptor thereby reducing its translation.

This invention further provides a transgenic nonhuman mammal comprising a homologous recombination knockout of the native Y2 receptor.

This invention provides a method for determining whether a ligand not known to be capable of binding to a human Y2 receptor can bind to a human Y2 receptor which comprises contacting a mammalian cell comprising an isolated DNA molecule encoding a human Y2 receptor with the ligand under conditions permitting binding of ligands known to bind to a Y2 receptor, detecting the presence of any of the ligand bound to a human Y2 receptor, and thereby determining whether the ligand binds to a human Y2 receptor.

This invention also provides a method for determining whether a ligand not known to be a human Y2 receptor agonist is capable of binding to the human Y2 receptor and functionally activate the human Y2 receptor which comprises contacting a mammalian cell expressing the human Y2 receptor with the ligand under conditions permitting the activation of a functional response, detecting an increase in Y2 receptor activity, and thereby determining whether the ligand is a human Y2 receptor agonist.

This invention further provides a method for determining whether a ligand not known to be a human Y2 receptor antagonist is capable of binding to the human Y2 receptor and functionally inhibit the human Y2 receptor activity which comprises contacting a mammalian cell expressing the human Y2 receptor with the ligand under conditions permitting the activation of a functional response, detecting a decrease in Y2 receptor activity, and thereby determining whether the ligand is a human Y2 receptor antagonist.

This invention further provides a method of screening drugs to identify drugs which specifically interact with, and bind to, the human Y2 receptor on the surface of a cell which comprises contacting a mammalian cell comprising an isolated DNA molecule encoding a human Y2 receptor with a plurality of drugs, determining those drugs which bind to the mammalian cell, and thereby identifying drugs which specifically interact with, and bind to, a human Y2 receptor.

This invention also provides a method of screening drugs to identify which act as agonists of the human Y2 receptor on the surface of a cell which comprises contacting a mammalian cell expressing human Y2 receptor with a plurality of drugs, determining those drugs which activate the receptor in the mammalian cell and thereby identifying drugs which specifically interact with, and activate the human Y2 receptor.

This invention also provides a method of screening drugs to identify drugs which act as antagonists of the human Y2 receptor on the surface of a cell which comprises contacting a mammalian cell expressing the human Y2 receptor with a plurality of drugs in the presence of a known human Y2 receptor agonist such as NPY, determining those drugs which inhibit the activation of the receptor in the mammalian cell, and thereby identifying drugs which act as antagonists of the human Y2 receptor.

This invention also provides a method of detecting expression of the Y2 receptor on the surface of a cell by detecting the presence of mRNA coding for a Y2 receptor which comprises obtaining total mRNA from the cell and contacting the mRNA so obtained with a nucleic acid probe comprising a nucleic acid molecule of at least 15 nucleotides capable of specifically hybridizing with a unique sequence included within the sequence of a nucleic acid molecule encoding a human Y2 receptor under hybridizing conditions, detecting the presence of mRNA hybridized to the probe, and thereby detecting the expression of the Y2 receptor by the cell.

This invention provides a method of determining the physiological effects of expressing varying levels of human Y2 receptors which comprises producing a transgenic nonhuman animal whose levels of human Y2 receptor expression are varied by use of an inducible promoter which regulates human Y2 receptor expression.

This invention also provides a method of determining the physiological effects of expressing varying levels of human Y2 receptors which comprises producing a panel of transgenic nonhuman animals each expressing a different amount of human Y2 receptor.

This invention also provides a method of determining the physiological effects of expressing varying levels of a human Y2 receptor which comprises producing a panel of transgenic nonhuman animals each expressing a different amount of the receptor.

This invention also provides a method of determining the physiological effects of expressing varying levels of a receptor which comprises producing a transgenic nonhuman animal whose levels of human Y2 receptor expression are varied by use of an inducible promoter which regulates receptor expression.

This invention provides a method for diagnosing a predisposition to a disorder associated with the expression of a specific human Y2 receptor allele which comprises: a. obtaining DNA of subjects suffering from the disorder; b. performing a restriction digest of the DNA with a panel of restriction enzymes; c. electrophoretically separating the resulting DNA fragments on a sizing gel; d. contacting the resulting gel with a nucleic acid probe capable of specifically hybridizing to DNA encoding a human Y2 receptor and labelled with a detectable marker; e. detecting labelled bands which have hybridized to the DNA encoding a human Y2 receptor labelled with a detectable marker to create a unique band pattern specific to the DNA of subjects suffering from the disorder; f. preparing DNA obtained for diagnosis by steps a–e; and g. comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method of preparing the isolated Y2 receptor which comprises inducing cells to express Y2 receptor, recovering the receptor from the resulting cells and purifying the receptor so recovered.

This invention also provides a method of preparing the isolated Y2 receptor which comprises inserting nucleic acid encoding Y2 receptor in a suitable vector, inserting the resulting vector in a suitable host cell, recovering the receptor produced by the resulting cell, and purifying the receptor so recovered.

BRIEF DESCRIPTION OF THE DRAWINGS

FIG. 1

Nucleotide sequence of the human hippocampal Y2 cDNA clone (SEQ. I.D. No. 1). Initiation and stop codon are indicated in bold. Only partial 5' and 3' untranslated sequences are shown.

FIG. 2

Deduced amino acid sequence of the human hippocampal Y2 cDNA clone encoded by the nucleotide sequence in FIG. 1. (SEQ. I.D. No. 2).

FIG. 3A through 3D

Comparison of coding nucleotide sequences between human hippocampal Y2 (top row) and Y1 human cDNA clones (bottom row) (48.5% nucleotide identity).

FIG. 4A through 4B

Comparison of amino acid sequences between hippocampal Y2 (top row) and Y1 human cDNA clones (bottom row). (31% overall identity and 41% in the transmembrane domains).

FIG. 5A

Equilibrium binding of $^{125}$I-PYY to membranes from COS-7 cells transiently expressing CG-13 (●) and human Y1 (○) receptors. Membranes were incubated with $^{125}$-PYY for the times indicated, in the presence or absence of 100 nM human NPY. Specific binding, B, was plotted against time, t, to obtain the maximum number of equilibrium binding sites, $B_1$ and $B_2$, and observed association rates, $K_{obs1}$ and $K_{obs2}$, according to the equation, $B=B_1*(1-e^{-(kobs1*t)})+B_2*(1-e^{-(kobs2*t)})$. Binding is shown as the percentage of total equilibrium binding, $B_1+B_2$, determined by nonlinear regression analysis. Data are representative of three independent experiments, with each point measured in triplicate.

FIG. 5B

Figure 5A:
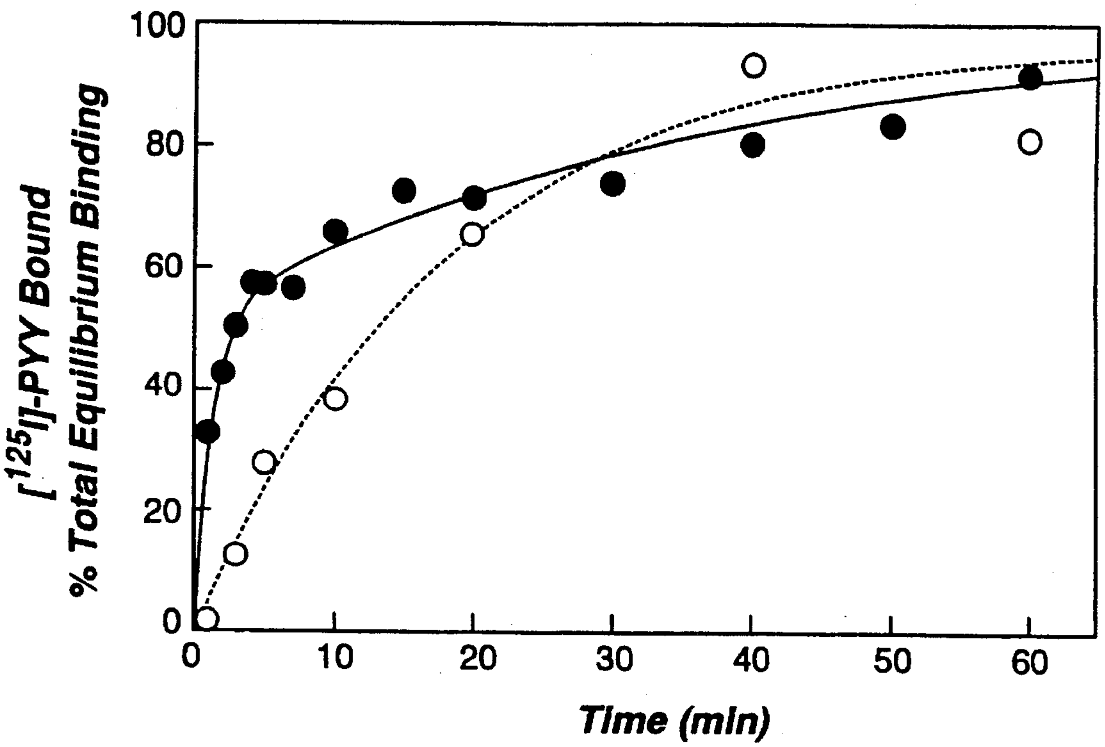
Figure 5B:
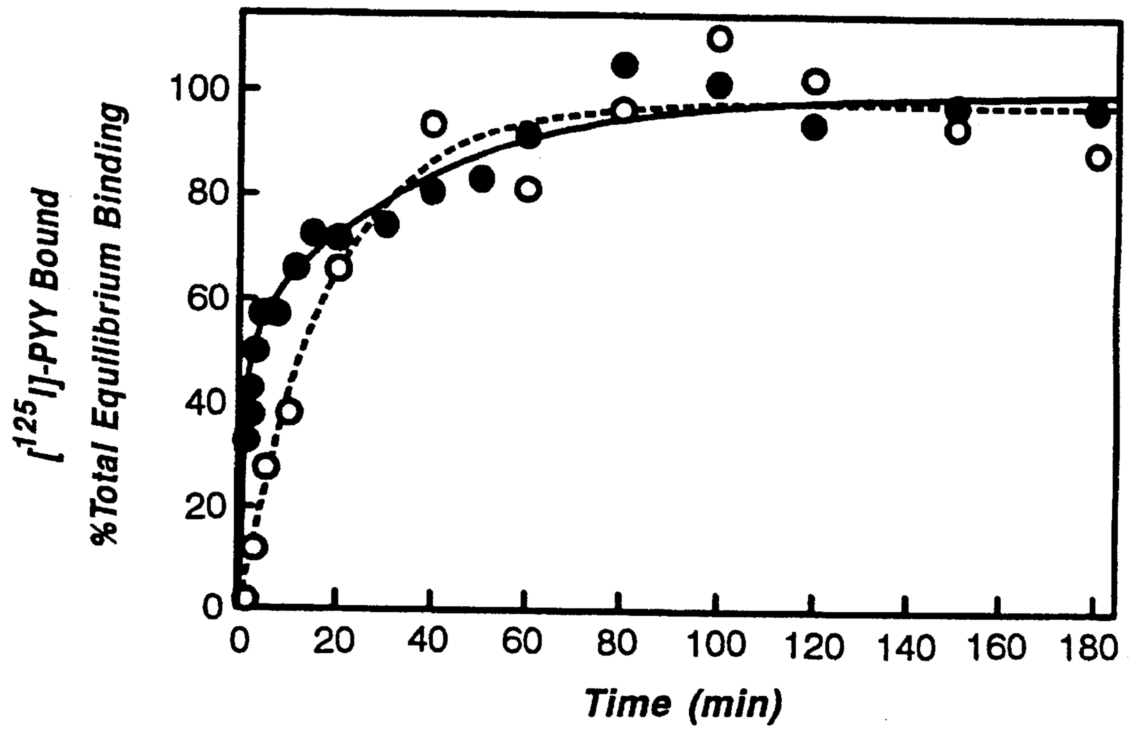

Equilibrium binding of $^{125}$I-PYY to membranes from COS-7 cells transiently expressing CG-13 (●) and human Y1 (○) receptors using the same conditions as in FIG. 5A except for a prolonged time course of up to 180 minutes.

FIG. 6

Saturable equilibrium binding of $^{125}$I-PYY to membranes from COS-7 cells transiently expressing CG-13 receptors. Membranes were incubated with $^{125}$I-PYY ranging in concentration from 0.003 nM to 2 nM, in the presence or absence of 100 nM human NPY. Specific binding, B, was plotted against the free $^{125}$I-PYY concentration, [L], to obtain the maximum number of saturable binding sites, $B_{max}$, and the $^{125}$I-PYY equilibrium dissociation constant, $K_d$, according to the binding isotherm, $B=B_{max}[L]/([L]+K_d)$. Specific binding is shown. Data are representative of three independent experiments, with each point measured in triplicate.

FIG. 7A

Competitive displacement of $^{125}$I-PYY on membranes from COS-7 cells transiently expressing Human Y1 receptors. Membranes were incubated with $^{125}$I-PYY and increasing concentrations of peptide competitors. $IC_{50}$ values corresponding to 50% displacement were determined by nonlinear regression analysis and converted to $K_i$ values according to the equation, $K_i=IC_{50}/(1+[L]/K_d)$, where [L] is the $^{125}$I-PYY concentration and $K_d$ is the equilibrium dissociation constant of $^{125}$I-PYY. Data are representative of at least two independent experiments, with each point measured once or in duplicate. Rank orders of affinity for these and other compounds are listed separately in Table 2.

FIG. 7B

Competitive displacement of $^{125}$I-PYY on membranes from COS-7 cells transiently expressing human Y2 receptors. Membranes were incubated with $^{125}$I-PYY and increasing concentrations of peptide competitors. $IC_{50}$ values corresponding to 50% displacement were determined by nonlinear regression analysis and converted to $K_i$ values according to the equation, $K_i=IC_{50}/(1+[L]/K_d)$, where [L] is the $^{125}$I-PYY concentration and $K_d$ is the equilibrium dissociation constant of $^{125}$I-PYY. Data are representative of at least two independent experiments, with each point measured once or in duplicate. Rank orders of affinity for these and other compounds are listed separately in Table 2.

DETAILED DESCRIPTION OF THE INVENTION

This invention provides isolated nucleic acid molecules which encode the human Y2 receptor. As used herein, the term Y2 receptor encompasses any amino acid sequence, polypeptide or protein having substantially the same pharmacology provided subject human Y2 receptor as shown in Tables 2–3 and FIGS. 5A–7B. As described herein our cloned receptor has a Y2 pharmacological profile that differs from the NPY receptor subtypes Y1 and Y3, PYY receptor, and PP receptor, and is therefore designated as the human Y2 receptor.

The only NPY receptor which has been cloned to date is the Y1 receptor gene, from mouse (Eva et al., 1992), rat (Eva et al., 1990), and human (Larhammar et al., 1992). The Y2 receptor's greatest homology with any known receptor disclosed in the Genbank/EMBL databases is a 42% overall amino acid identity with the human Y1 receptor.

This invention provides an isolated nucleic acid molecule encoding a human Y2 receptor. As used herein, the term "isolated nucleic acid molecule" means a nucleic acid molecule that is a molecule in a form which does not occur in nature. Examples of such an isolated nucleic acid molecule are an RNA, cDNA, or isolated genomic DNA molecule encoding a human Y2 receptor. The human Y2 receptor has an amino acid sequence substantially the same as the deduced amino acid sequence shown in FIG. 2 and any human receptor having substantially the same amino acid sequence as shown in FIG. 2 is by definition a human Y2 receptor. One means of isolating a human Y2 receptor is to probe a human genomic library with a natural or artificially designed DNA probe, using methods well known in the art. DNA probes derived from the human receptor gene Y2 are particularly useful probes for this purpose. DNA and cDNA molecules which encode human Y2 receptors may be used to obtain complementary genomic DNA, cDNA or RNA from human, mammalian or other animal sources, or to isolate related cDNA or genomic clones by the screening of cDNA or genomic libraries by methods described in more detail below. Transcriptional regulatory elements from the 5' untranslated region of the isolated clones, and other stability, processing, transcription, translation, and tissue specificity-determining regions from the 3' and 5' untranslated regions of the isolated genes are thereby obtained. Examples of a nucleic acid molecule are an RNA, cDNA, or isolated genomic DNA molecule encoding a human Y2 receptor. Such molecules may have coding sequences substantially the same as the coding sequence shown in FIG. 1. The DNA molecule of FIG. 1 encodes the sequence of the human Y2 receptor gene.

This invention further provides a cDNA molecule of encoding a human Y2 receptor having a coding sequence substantially the same as the coding sequence shown in FIG. 1. This molecule is obtained by the means described above.

This invention also provides an isolated protein which is a human Y2 receptor. As used herein, the term "isolated protein means a protein molecule free of other cellular components. An example of such protein is an isolated protein having substantially the same amino acid sequence as the amino acid sequence shown in FIG. 2 which is a human Y2 receptor. One means for obtaining isolated Y2 receptor is to express DNA encoding the receptor in a suitable host, such as a bacterial, yeast, insect or mammalian cell, using methods well known in the art, and recovering the receptor protein after it has been expressed in such a host, again using methods well known in the art. The receptor may also be isolated from cells which express it, in particular from cells which have been transfected with the expression vectors described below in more detail.

This invention provides a vector comprising an isolated nucleic acid molecule such as DNA, RNA, or cDNA encoding a human Y2 receptor. Examples of vectors are viruses such as bacteriophages (such as phage lambda), animal viruses (such as Herpes virus, Murine Leukemia virus, and Baculovirus), cosmids, plasmids (such as pUC18, available from Pharmacia, Piscataway, N.J.), and other recombination vectors. Nucleic acid molecules are inserted into vector genomes by methods well known in the art. For example, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available. A specific example of such plasmids is a plasmid comprising cDNA having a coding sequence substantially the same as the coding sequence shown in FIG. 1 and designated clone CG-13 (Seq. I.D. No. 1).

This invention also provides vectors comprising a DNA molecule encoding a human Y2 receptor, adapted for expression in a bacterial cell, a yeast cell, insect or a mammalian cell which additionally comprise the regulatory elements necessary for expression of the DNA in the bacterial, yeast, insect or mammalian cells operatively linked to the DNA encoding a human Y2 receptor as to permit expression thereof. DNA having coding sequences substantially the same as the coding sequence shown in FIG. 1 may usefully be inserted into the vectors to express human Y2 receptors. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Furthermore, an insect expression vector, such as recombinant baculovirus, uses the polyhedron gene expression signals for expression of the inserted gene in insect cells. Such vectors may be obtained commercially or assembled from the sequences described by methods well known in the art, for example the methods described above for constructing vectors in general. Expression vectors are useful to produce cells that express the receptor. Certain uses for such cells are described in more detail below.

This invention further provides a plasmid adapted for expression in a bacterial, yeast, insect, or, in particular, a mammalian cell which comprises a DNA molecule encoding a human Y2 receptor and the regulatory elements necessary for expression of the DNA in the bacterial, yeast, insect, or mammalian cell operatively linked to the DNA encoding a human Y2 receptor as to permit expression thereof. Some plasmids adapted for expression in a mammalian cell are pSVL (available from Pharmacia, Piscataway, N.J.) and pcEXV-3 (73). A specific example of such plasmid is a plasmid adapted for expression in a mammalian cell comprising cDNA having coding sequences substantially the same as the coding sequence shown in FIG. 1 and the regulatory elements necessary for expression of the DNA in the mammalian cell which is designated pcEXV-hY2 and deposited under ATCC Accession No. 75659, deposited on Jan. 27, 1994. Those skilled in the art will readily appreciate that numerous plasmids adapted for expression in a mammalian cell which comprise DNA of encoding human Y2 receptors and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

The deposit discussed supra, and the other deposits discussed herein, were made pursuant to, and in satisfaction of, the Budapest Treaty on the International Recognition of the Deposit of Microorganisms for the Purpose of Patent Procedure with the American Type Culture Collection (ATCC), 12301 Parklawn Drive, Rockville, Md. 20852.

This invention provides a mammalian cell comprising a DNA molecule encoding a human Y2 receptor, such as a mammalian cell comprising a plasmid adapted for expression in a mammalian cell, which comprises a DNA molecule encoding a human Y2 receptor, the protein encoded thereby is expressed on the cell surface, and the regulatory elements necessary for expression of the DNA in the mammalian cell operatively linked to the DNA encoding a human Y2 receptor as to permit expression thereof. Numerous mammalian cells may be used as hosts, including, for example, the mouse fibroblast cell NIH3T3, CHO cells, HeLa cells, L-M(TK-) cells, etc. Expression plasmids such as that described supra may be used to transfect mammalian cells by methods well known in the art such as calcium phosphate precipitation, or DNA encoding these Y2 receptors may be otherwise introduced into mammalian cells, e.g., by microinjection, to obtain mammalian cells which comprise DNA, e.g., cDNA or a plasmid, encoding either human Y2 receptor. A specific example of such cells is a cell comprising the pcEXV-hY2 plasmid adapted for expression in a mammalian cell comprising cDNA encoding the Y2 receptor and the regulatory elements necessary for expression of the DNA in the mammalian cell which is designated 293-hY2-10 and deposited under ATCC Accession No. CRL 11537, deposited on Jan. 27, 1994.

This invention provides a method for determining whether a ligand not known to be capable of binding to a human Y2 receptor can bind to a human Y2 receptor which comprises contacting a mammalian cell comprising a DNA molecule encoding a human Y2 receptor, the protein encoded thereby is expressed on the cell surface, with the ligand under conditions permitting binding of ligands known to bind to the Y2 receptor, detecting the presence of any of the ligand bound to the Y2 receptor, and thereby determining whether the ligand binds to the Y2 receptor. This invention also provides a method for determining whether a ligand not known to be capable of binding to the human Y2 receptor can act as a human Y2 receptor agonist. As used herein, the term "agonist" means any ligand capable of increasing human Y2 receptor normal functional activity. This comprises contacting a mammalian cell comprising an isolated DNA molecule which encodes a human Y2 receptor with the ligand under conditions permitting the activation of a functional response, detected an increase in Y2 receptor activity, and thereby determining which ligands act as a human Y2 receptor agonist. This invention also provides a method for determining whether a ligand not known to be capable of binding to the human Y2 receptor can act as a human Y2 receptor antagonist. As used herein, the term "antagonist" means any ligand capable of inhibiting Y2 receptor normal functional activity. This comprises contacting a mammalian cell comprising an isolated DNA molecule which encodes a human Y2 receptor with the ligand and a known human Y2 receptor agonist such as PYY, under conditions permitting the activation of a functional response, detecting a decrease in human Y2 receptor activity, and thereby determining which ligands act as human Y2 receptor antagonists. The DNA in the mammalian cell may have a coding sequence substantially the same as the coding sequence shown in FIG. 1. Preferably, the mammalian cell is nonneuronal in origin. An example of a nonneuronal mammalian cell is a COS-7 cell. Other examples of a non-neuronal mammalian cells that can be used for functional assays with human receptors are the 293 human embryonic kidney cells and L-M(TK-) cells. The preferred method for determining whether a ligand is capable of binding to the human Y2 receptor comprises contacting a transfected nonneuronal mammalian cell (i.e. a cell that does not naturally express any type of NPY, PP, or PYY receptor, thus will only express such a receptor if it is transfected into the cell) expressing a Y2 receptor on its surface, or contacting a membrane preparation derived from such a transfected cell, with the ligand under conditions which are known to prevail, and thus to be associated with, in vivo binding of the ligand to a Y2 receptor, detecting the presence of any of the ligand being tested bound to the Y2 receptor on the surface of the cell, and thereby determining whether the ligand binds to, activates or inhibits the activation of the Y2 receptor. This response system is obtained by transfection of isolated DNA into a suitable host cell containing the desired second messenger system such as phospholipase C, adenylate cyclase, guanylate cyclase or ion channels. Such a host system is isolated from pre-existing cell lines, or can be generated by inserting appropriate components of second messenger systems into existing cell lines. Such a transfection system provides a complete response system for investigation or assay of the activity of human Y2 receptors with ligands as described above. Transfection systems are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for these competitive binding assays. Functional assays of signal transduction pathways in transfection systems determine a ligand's efficacy of activating the receptor. A transfection system constitutes a "drug discovery system" useful for the identification of natural or synthetic compounds with potential for drug development that can be further modified or used directly as therapeutic compounds to activate or inhibit the natural functions of the human Y2 receptor. The transfection system is also useful for determining the affinity and efficacy of known drugs at the human Y2 receptor sites.

This invention also provides a method of screening drugs to identify drugs which specifically interact with, and bind to, the human Y2 receptor on the surface of a cell which comprises contacting a mammalian cell comprising a DNA molecule encoding a human Y2 receptor on the surface of a cell with a plurality of drugs, determining those drugs which bind to the mammalian cell, and thereby identifying drugs which specifically interact with, and bind to, the human Y2 receptor. This invention also provides a method of screening drugs to identify drugs which interact with, and act as human Y2 receptor agonists which comprises contacting the mammalian cell comprising an isolated DNA molecule encoding and expressing a human Y2 receptor with a plurality of drugs under conditions permitting the activation of a functional human Y2 receptor response, determining those drugs which activate the human Y2 receptor in the mammalian cell, and thereby identifying drugs which specifically interact with, and act as a human Y2 receptor agonist. This invention also provides a method of screening drugs to identify drugs which interact with and act as a human Y2 receptor antagonist which comprises contacting the mammalian cell comprising an isolated DNA molecule encoding and expressing a human Y2 receptor with a plurality of drugs in the presence of a known Y2 receptor agonist such as PYY under conditions permitting the activation of a functional human Y2 receptor response, determining those drugs which inhibit the human Y2 receptor in the mammalian cell, and thereby identifying drugs which specifically interact with, and act as a human Y2 receptor antagonist. The DNA in the cell may have a coding sequence substantially the same as the coding sequence shown in FIG. 1. Preferably, the mammalian cell is nonneuronal in origin. An example of a nonneuronal mammalian cell is an COS-7 cell. Other examples of a non-neuronal mammalian cell to be used for functional assays are 293 human embryonic kidney cells and L-M(TK-) cells. Drug candidates are identified by choosing chemical compounds which bind with high affinity to the expressed Y2 receptor protein in transfected cells, using radioligand binding methods well known in the art, examples of which are shown in the binding assays described herein. Drug candidates are also screened for selectivity by identifying compounds which bind with high affinity to the human Y2 receptor but do not bind with high affinity to any other NPY receptor subtype or to any other known receptor site. Because selective, high affinity compounds interact primarily with the target Y2 receptor site after administration to the patient, the chances of producing a drug with unwanted side effects are minimized by this approach. This invention provides a pharmaceutical composition comprising a drug identified by the method described above and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bio-available, in an appropriate solid or solution formulation, to gain the desired therapeutic benefit.

This invention provides a nucleic acid probe comprising a nucleic acid molecule of at least 15 nucleotides capable of specifically hybridizing with a unique sequence included within the sequence of a nucleic acid molecule encoding a human Y2 receptor, for example with a coding sequence included within the sequence shown in FIG. 1. As used herein, the phrase "specifically hybridizing" means the ability of a nucleic acid molecule to recognize a nucleic acid sequence complementary to its own and to form double-helical segments through hydrogen bonding between complementary base pairs. As used herein, a "unique sequence" is a sequence specific to only the nucleic acid molecules encoding the human Y2 receptor. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding human Y2 receptors is useful as a diagnostic test for any disease process in which levels of expression of the corresponding Y2 receptor is altered. DNA probe molecules are produced by insertion of a DNA molecule which encodes human Y2 receptor or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. An example of such DNA molecule is shown in FIG. 1. The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes human Y2 receptor are useful as probes for these genes, for their associated mRNA, or for the isolation of related genes by homology screening of genomic or cDNA libraries, or by the use of amplification techniques such as the Polymerase Chain Reaction. Synthesized oligonucleotides as described may also be used to determine the cellular localization of the mRNA produced by the Y2 gene by in situ hybridization.

This invention also provides a method of detecting expression of a Y2 receptor on the surface of a cell by detecting the presence of mRNA coding for a Y2 receptor which comprises obtaining total mRNA from the cell using methods well known in the art and contacting the mRNA so obtained with a nucleic acid probe comprising a nucleic acid molecule of at least 15 nucleotides capable of specifically hybridizing with a sequence included within the sequence of a nucleic acid molecule encoding a human Y2 receptor under hybridizing conditions, detecting the presence of mRNA hybridized to the probe, and thereby detecting the expression of the Y2 receptor by the cell. Hybridization of probes to target nucleic acid molecules such as mRNA molecules employs techniques well known in the art. In one possible means of performing this method, nucleic acids are extracted by precipitation from lysed cells and the mRNA is isolated from the extract using a column which binds the poly-A tails of the mRNA molecules. The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of specifically hybridizing with any sequences of an mRNA molecule which encodes a human Y2 receptor so as to prevent translation of the mRNA molecule. The antisense oligonucleotide may have a sequence capable of specifically hybridizing with any sequences of the cDNA molecule whose sequence is shown in FIG. 1. A particular example of an antisense oligonucleotide is an antisense oligonucleotide comprising chemical analogues of nucleotides.

This invention also provides a pharmaceutical composition comprising an amount of the oligonucleotide described above effective to reduce expression of a human Y2 receptor by passing through a cell membrane and specifically hybridizing with mRNA encoding a human Y2 receptor in the cell so as to prevent its translation and a pharmaceutically acceptable hydrophobic carrier capable of passing through a cell membrane. The oligonucleotide may be coupled to a substance which inactivates mRNA, such as a ribozyme. The pharmaceutically acceptable hydrophobic carrier capable of passing through cell membranes may also comprise a structure which binds to a receptor specific for a selected cell type and is thereby taken up by cells of the selected cell type. The structure may be part of a protein known to bind a cell-type specific receptor, for example an insulin molecule, which would target pancreatic cells. DNA molecules having coding sequences substantially the same as the coding sequence shown in FIG. 1 may be used as the oligonucleotides of the pharmaceutical composition.

This invention also provides a method of treating abnormalities which are alleviated by reduction of expression of a Y2 receptor which comprises administering to a subject an amount of the pharmaceutical composition described above effective to reduce expression of the Y2 receptor by the subject. This invention further provides a method of treating an abnormal condition related to Y2 receptor activity which comprises administering to a subject an amount of the pharmaceutical composition described above effective to reduce expression of the Y2 receptor by the subject. Several examples of such abnormal conditions are hypertension, gastrointestinal disorders, epilepsy, pain, sleep disorders, cognitive disorders, and nasal congestion (58–80).

Antisense oligonucleotide drugs inhibit translation of mRNA encoding these receptors. Synthetic oligonucleotides, or other antisense chemical structures are designed to bind to mRNA encoding the Y2 receptor and inhibit translation of mRNA and are useful as drugs to inhibit expression of Y2 receptor genes in patients. This invention provides a means to therapeutically alter levels of expression of human Y2 receptors by the use of a synthetic antisense oligonucleotide drug (SAOD) which inhibits translation of mRNA encoding these receptors. Synthetic oligonucleotides, or other antisense chemical structures designed to recognize and selectively bind to mRNA, are constructed to be complementary to portions of the nucleotide sequences shown in FIG. 1 of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g. by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which binds and takes up the SAOD only within certain selected cell populations. For example, the SAOD may be designed to bind to a receptor found only in a certain cell type, as discussed above. The SAOD is also designed to recognize and selectively bind to the target mRNA sequence, which may correspond to a sequence contained within the sequence shown in FIG. 1 by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (74,75). In addition, coupling of ribozymes to antisense oligonucleotides is a promising strategy for inactivating target mRNA (76). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce receptor expression in particular target cells of a patient, in any clinical condition which may benefit from reduced expression of Y2 receptors.

This invention provides an antibody directed to the human Y2 receptor, for example a monoclonal antibody directed to an epitope of a human Y2 receptor present on the surface of a cell and having an amino acid sequence substantially the same as an amino acid sequence for a cell surface epitope of the human Y2 receptor included in the amino acid sequence shown in FIG. 2 (Seq. I.D. No. 2). Amino acid sequences may be analyzed by methods well known in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIG. 2 will probably bind to a surface epitope of a human Y2 receptor, as described. Antibodies directed to human Y2 receptors may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as COS-7 cells or L-M(TK-) cells comprising DNA encoding the human Y2 receptor and thereby expressing the human Y2 receptor may be used as immunogens to raise such an antibody. Alternatively, synthetic peptides may be prepared using commercially available machines and the amino acid sequence shown in FIG. 2 (Seq. I.D. No. 2). As a still further alternative, DNA, such as a cDNA or a fragment thereof, may be cloned and expressed and the resulting polypeptide recovered and used as an immunogen. These antibodies are useful to detect the presence of human Y2 receptors encoded by the isolated DNA, or to inhibit the function of the receptors in living animals, in humans, or in biological tissues or fluids isolated from animals or humans.

This invention provides a pharmaceutical composition which comprises an amount of an antibody directed to the human Y2 receptor effective to block binding of naturally occurring ligands to the Y2 receptor, and a pharmaceutically acceptable carrier. A monoclonal antibody directed to an epitope of a human Y2 receptor present on the surface of a cell and having an amino acid sequence substantially the same as an amino acid sequence for a cell surface epitope of the human Y2 receptor included in the amino acid sequence shown in FIG. 2 is useful for this purpose.

This invention also provides a method of treating abnormalities which are alleviated by reduction of expression of a human Y2 receptor which comprises administering to a subject an amount of the pharmaceutical composition described above effective to block binding of naturally occurring ligands to the Y2 receptor and thereby alleviate abnormalities resulting from overexpression of a human Y2 receptor. Binding of the antibody to the receptor prevents the receptor from functioning, thereby neutralizing the effects of overexpression. The monoclonal antibodies described above are both useful for this purpose. This invention additionally provides a method of treating an abnormal condition related to an excess of Y2 receptor activity which comprises administering to a subject an amount of the pharmaceutical composition described above effective to block binding of naturally occurring ligands to the Y2 receptor and thereby alleviate the abnormal condition. Some examples of abnormal conditions are hypertension, gastrointestinal disorders, epilepsy, pain, sleep disorders, cognitive disorders, and nasal congestion (58–72).

This invention provides a method of detecting the presence of a Y2 receptor on the surface of a cell which comprises contacting the cell with an antibody directed to the human Y2 receptor, under conditions permitting binding of the antibody to the receptor, detecting the presence of the antibody bound to the cell, and thereby the presence of the human Y2 receptor on the surface of the cell. Such a method is useful for determining whether a given cell is defective in expression of Y2 receptors on the surface of the cell. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal expressing DNA encoding a human Y2 receptor. This invention also provides a transgenic nonhuman mammal comprising a homologous recombination knockout of the native Y2 receptor. This invention also provides a transgenic nonhuman mammal whose genome comprises antisense DNA complementary to DNA encoding a human Y2 receptor so placed as to be transcribed into antisense mRNA which is complementary to mRNA encoding a Y2 receptor and which hybridizes to mRNA encoding a Y2 receptor thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequence shown in FIG. 1. An example of a transgenic animal is a transgenic mouse. Examples of tissue specificity-determining regions are the metallothionein promotor (77) and the L7 promotor (78).

Animal model systems which elucidate the physiological and behavioral roles of human Y2 receptors are produced by creating transgenic animals in which the expression of a Y2 receptor is either increased or decreased, or the amino acid sequence of the expressed Y2 receptor protein is altered, by a variety of techniques. Examples of these techniques include: 1) Insertion of normal or mutant versions of DNA encoding a human Y2 receptor or homologous animal versions of these genes, by microinjection, retroviral infection or other means well known to those skilled in the art, into appropriate fertilized embryos in order to produce a transgenic animal (79). 2) Homologous recombination (80, 81) of mutant or normal, human or animal versions of these genes with the native gene locus in transgenic animals to alter the regulation of expression or the structure of these Y2 receptors. The technique of homologous recombination is well known in the art. It replaces the native gene with the inserted gene and so is useful for producing an animal that cannot express native receptor but does express, for example, an inserted mutant receptor, which has replaced the native receptor in the animal's genome by recombination, resulting in underexpression of the receptor. Microinjection adds genes to the genome, but does not remove them, and so is useful for producing an animal which expresses its own and added receptors, resulting in overexpression of the receptor. One means available for producing a transgenic animal, with a mouse as an example, is as follows: Female mice are mated, and the resulting fertilized eggs are dissected out of their oviducts. The eggs are stored in an appropriate medium such as M2 medium (79). DNA or cDNA encoding a human Y2 receptor is purified from a vector (such as plasmid pcEXV-Y2 described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of receptor-specific drugs is to activate or to inhibit the receptor, the transgenic animal model systems described above are useful for testing the biological activity of drugs directed against these Y2 receptors even before such drugs become available. These animal model systems are useful for predicting or evaluating possible therapeutic applications of drugs which activate or inhibit these human Y2 receptors by inducing or inhibiting expression of the native or trans-gene and thus increasing or decreasing expression of normal or mutant human Y2 receptors in the living animal. Thus, a model system is produced in which the biological activity of drugs directed against these Y2 receptors are evaluated before such drugs become available. The transgenic animals which over or under produce the human Y2 receptor indicate by their physiological state whether over or under production of the human Y2 receptor is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less receptor by the affected cells, leading eventually to underexpression. Therefore, an animal which underexpresses receptor is useful as a test system to investigate whether the actions of such drugs which result in under expression are in fact therapeutic. Another use is that if overexpression is found to lead to abnormalities, then a drug which downregulates or acts as an antagonist to Y2 receptor is indicated as worth developing, and if a promising therapeutic application is uncovered by these animal model systems, activation or inhibition of the Y2 receptor is achieved therapeutically either by producing agonist or antagonist drugs directed against these Y2 receptors or by any method which increases or decreases the expression of these Y2 receptors in man.

This invention provides a method of determining the physiological effects of expressing varying levels of human Y2 receptors which comprises producing a transgenic nonhuman animal whose levels of human Y2 receptor expression are varied by use of an inducible promoter which regulates human Y2 receptor expression. This invention also provides a method of determining the physiological effects of expressing varying levels of human Y2 receptors which comprises producing a panel of transgenic nonhuman animals each expressing a different amount of human Y2 receptor. Such animals may be produced by introducing different amounts of DNA encoding a human Y2 receptor into the oocytes from which the transgenic animals are developed.

This invention also provides a method for identifying a substance capable of alleviating abnormalities resulting from overexpression of a human Y2 receptor comprising administering the substance to a transgenic nonhuman mammal expressing at least one artificially introduced DNA molecule encoding a human Y2 receptor and determining whether the substance alleviates the physical and behavioral abnormalities displayed by the transgenic nonhuman mammal as a result of overexpression of a human Y2 receptor. As used herein, the term "substance" means a compound or composition which may be natural, synthetic, or a product derived from screening. Examples of DNA molecules are DNA or cDNA molecules having a coding sequence substantially the same as the coding sequence shown in FIG. 1.

This invention provides a pharmaceutical composition comprising an amount of the substance described supra effective to alleviate the abnormalities resulting from overexpression of Y2 receptor and a pharmaceutically acceptable carrier.

This invention further provides a method for treating the abnormalities resulting from overexpression of a human Y2 receptor which comprises administering to a subject an amount of the pharmaceutical composition described above effective to alleviate the abnormalities resulting from overexpression of a human Y2 receptor.

This invention provides a method for identifying a substance capable of alleviating the abnormalities resulting from underexpression of a human Y2 receptor comprising administering the substance to the transgenic nonhuman mammal described above which underexpresses human Y2 receptor and determining whether the substance alleviates the physical and behavioral abnormalities displayed by the transgenic nonhuman mammal as a result of underexpression of a human Y2 receptor.

This invention also provides a pharmaceutical composition comprising an amount of a substance effective to alleviate abnormalities resulting from underexpression of Y2 receptor and a pharmaceutically acceptable carrier.

This invention further provides a method for treating the abnormalities resulting from underexpression of a human Y2 receptor which comprises administering to a subject an amount of the pharmaceutical composition described above effective to alleviate the abnormalities resulting from underexpression of a human Y2 receptor.

This invention provides a method for diagnosing a predisposition to a disorder associated with the expression of a specific human Y2 receptor allele which comprises: a) obtaining DNA of subjects suffering from the disorder; b) performing a restriction digest of the DNA with a panel of restriction enzymes; c. electrophoretically separating the resulting DNA fragments on a sizing gel; d) contacting the resulting gel with a nucleic acid probe capable of specifically hybridizing to DNA encoding a human Y2 receptor and labelled with a detectable marker; e) detecting labelled bands which have hybridized to the DNA encoding a human Y2 receptor labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific human Y2 receptor allele.

This invention provides a method of preparing the isolated Y2 receptor which comprises inducing cells to express Y2 receptor, recovering the receptor from the resulting cells, and purifying the receptor so recovered. An example of an isolated Y2 receptor is an isolated protein having substantially the same amino acid sequence as the amino acid sequence shown in FIG. 2. For example, cells can be induced to express receptors by exposure to substances such as hormones. The cells can then be homogenized and the receptor isolated from the homogenate using an affinity column comprising, for example, PYY or another substance which is known to bind to the receptor. The resulting fractions can then be purified by contacting them with an ion exchange column, and determining which fraction contains receptor activity or binds antireceptor antibodies.

This invention provides a method of preparing the isolated Y2 receptor which comprises inserting nucleic acid encoding Y2 receptor in a suitable vector, inserting the resulting vector in a suitable host cell, recovering the receptor produced by the resulting cell, and purifying the receptor so recovered. An example of an isolated Y2 receptor is an isolated protein having substantially the same amino acid sequence as the amino acid sequence shown in FIG. 2. This method for preparing Y2 receptor uses recombinant DNA technology methods well known in the art. For example, isolated nucleic acid encoding Y2 receptor is inserted in a suitable vector, such as an expression vector. A suitable host cell, such as a bacterial cell, or a eukaryotic cell such as a yeast cell, is transfected with the vector. Y2 receptor is isolated from the culture medium by affinity purification or by chromatography or by other methods well known in the art.

This invention provides an antisense oligonucleotide having a sequence capable of binding specifically with any sequences of an mRNA molecule which encodes a receptor so as to prevent translation of the mRNA molecule.

This invention also provides a transgenic nonhuman mammal expressing DNA encoding a human Y2 receptor.

This invention further provides a transgenic nonhuman mammal comprising a homologous recombination knockout of the native Y2 receptor.

This invention provides a method of determining the physiological effects of expressing varying levels of a receptor which comprises producing a transgenic nonhuman animal whose levels of receptor expression are varied by use of an inducible promoter which regulates receptor expression.

This invention also provides a method of determining the physiological effects of expressing varying levels of a receptor which comprises producing a panel of transgenic nonhuman animals each expressing a different amount of the receptor.

This invention further provides transgenic nonhuman mammal whose genome comprises antisense DNA complementary to DNA encoding a receptor so placed as to be transcribed into antisense mRNA which is complementary to mRNA encoding the receptor and which hybridizes to mRNA encoding the receptor thereby preventing its translation.

This invention provides a method for determining whether a ligand not known to be capable of binding to a receptor can bind to a receptor which comprises contacting a mammalian cell comprising an isolated DNA molecule encoding the receptor with the ligand under conditions permitting binding of ligands known to bind to a receptor, detecting the presence of any of the ligand bound to the receptor, and thereby determining whether the ligand binds to the receptor.

This invention identifies for the first time a new receptor protein, its amino acid sequence, and its human gene. Furthermore, this invention describes a previously unrecognized group of receptors within the definition of a Y2 receptor. The information and experimental tools provided by this discovery are useful to generate new therapeutic agents, and new therapeutic or diagnostic assays for this new receptor protein, its associated mRNA molecule or its associated genomic DNA. The information and experimental tools provided by this discovery will be useful to generate new therapeutic agents, and new therapeutic or diagnostic assays for this new receptor protein, its associated mRNA molecule, or its associated genomic DNA.

Specifically, this invention relates to the first isolation of a human genomic clone encoding a Y2 receptor. A new human gene for the receptor identified herein as Y2 has been identified and characterized. In addition, the human Y2 receptor has been expressed in 293 human embryonic kidney cells. The pharmacological binding properties of the protein encoded have been determined, and these binding properties classify this protein as a novel human NPY/PYY receptor which we designate as a human Y2 receptor. Mammalian cell lines expressing this human Y2 receptor at the cell surface have been constructed, thus establishing the first well-defined, cultured cell lines With which to study this Y2 receptor.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS cDNA Cloning

Total RNA was prepared by a modification of the guanidine thiocyanate method (13), from 6 grams of human hippocampus. Poly $A^+RNA$ was purified with a FastTrack kit (Invitrogen Corp., San Diego, Calif.). Double stranded (ds) cDNA was synthesized from 4 μg of poly $A^+RNA$ according to Gubler and Hoffman (14), except that ligase was omitted in the second strand cDNA synthesis. The resulting DS cDNA was ligated to BstxI/EcoRI adaptors (Invitrogen Corp.), the excess of adaptors was removed by chromatography on Sephacryl 500 HR (Pharmacia-LKB) and the ds-cDNA size selected by chromatography on Sephacryl 1000 (Pharmacia-LKB). High molecular weight fractions were ligated in pcEXV.BS (An Okayama and Berg expression vector) cut by BstxI as described by Aruffo and Seed (15). The ligated DNA was electroporated in *E. coli* MC 1061 (Gene Pulser, Biorad). A total of $2.2\times10^6$ independent clones with an insert mean size of 3 kb could be generated. The library was plated on Petri dishes (Ampicillin selection) in pools of 0.4 to $1.2\times10^4$ independent clones. After 18 hours amplification, the bacteria from each pool were scraped, resuspended in 4 ml of LB media and 1.5 ml processed for plasmid purification by the alkali method (16). 1 ml aliquots of each bacterial pool were stored at −85° C. in 20% glycerol.

Isolation of a cDNA clone encoding a human hippocampal Y2 receptor.

DNA from pools of ≈5000 independent clones was transfected into COS-7 cells by a modification of the DEAE-dextran procedure (17). COS-7 cells were grown in Dulbecco's Modified Eagle Medium (DMEM) supplemented with 10% fetal calf serum, 100 U/ml of penicillin, 100 μg/ml of streptomycin, 2 mM L-glutamine (DMEM-C) at 37° C. in 5% $CO_2$. The cells were seeded one day before transfection at a density of 30,000 cells/$cm^2$ in 6 well plates (Becton Dickinson, Lincoln Park, N.J.). On the next day, cells were washed twice with Phosphate Buffer Saline (PBS), 400 μl of transfection cocktail was added containing 1/10 of the DNA from each pool and DEAE-dextran (500 μg/ml) in PBS. After a 30 min. incubation at 37° C., 1.6 ml of chloroquine (80 μM in DMEM-C) was added and the cells incubated a further 2.5 hours at 37° C. The media was aspirated from each well and 1 ml of 10% DMSO in DMEM-C added. After 2.5 min. incubation at room temperature, the media was aspirated, each well washed once with 1 ml PBS and the cells incubated 24 hours in DMEM-C. The cells were then trypsinized and seeded on Lab-Tek chamber slides (1 chamber, Permanox slide from Nunc Inc., Naperville, Ill.), incubated in 2 ml DMEM-C for another 24 hours and the binding assay was performed on the slides.

After two washes with PBS, positive pools were identified by incubating the cells with 1 nM ($3\times10^6$ cpm per slide) of porcine [$^{125}$I]-PYY (New England Nuclear; specific activity=2200Ci/mmol) in 20 mM Hepes-NaOH pH 7.4, $CaCl_2$ 1.26 mM, $MgSO_4$ 0.81 mM, $KH_2PO_4$ 0.44 mM, $KCl_{5.4}$, NaCl 10 mM , 0.1% bovine serum albumin, 0.1% bacitracin for 1 hour at room temperature. After six washes (five seconds each) in binding buffer without ligand, the monolayers were fixed in 2.5% glutaraldehyde in PBS for five minutes, washed twice two minutes in PBS, dehydrated in ethanol baths for two minutes each (70, 80, 95, 100%) and air dried.

The slides were then dipped in 100% photoemulsion (Kodak type NTB2) at 42° C. and exposed in the dark for 48 hours at 4° C. in light proof boxes containing drierite. Slides were developed for three minutes in Kodak D19 developer (32 g/l of water), rinsed in water, fixed in Kodak fixer for 5 minutes, rinsed in water, air dried and mounted with Aqua-Mount (Lerner Laboratories, Pittsburgh, Pa.). Slides were screened at 25× total magnification.

A single clone, CG-13, was isolated by SIB selection as described (18). DS-DNA was sequenced with a Sequenase kit (US Biochemical, Cleveland, Ohio) according to the manufacturer. Nucleotide and peptide sequences analysis were performed with GCG programs (Genetics Computer group, Madison, Wis.).

DNA Transfection for Pharmacological Characterization

COS-7 cells were grown on 150 mm plates in D-MEM with supplements (Dulbecco's Modified Eagle Medium with 10% bovine calf serum, 2 mM glutamine, 100 units/ml penicillin 80 units/ml streptomycin) at 37° C., 5% $CO_2$. For transient expression, COS-7 cells were transfected by the DEAE-Dextran method, using 1 μg of DNA/$10^6$ cells (17).

Cell Culture

SK-N-Be(2) human neuroblastoma cells were grown similarly in 225 $cm^2$ flasks using 50% Eagle's Modified Essential Media, 50% Ham's Nutrient Mixture F-12, 15% fetal bovine serum, 2 mM glutamine, 100 units/ml penicillin/80 units/ml streptomycin, and 1% non-essential amino acids. Stock flasks of SK-N-Be(2) cells were trypsinized and split 1:10 every 7 days.

Membrane Preparation

Membranes were harvested from COS-7 cells 48 hours after transfection and from SK-N-Be(2) seven days after splitting. Adherent cells were washed twice in ice-cold phosphate buffered saline (138 mM NaCl, 8.1 mM $Na_2HPO_4$, 2.5 mM KCl, 1.2 mM $KH_2PO_4$, 0.9 mM $CaCl_2$, 0.5 mM $MgCl_2$, pH 7.4) and lysed by sonication in ice-cold hypotonic buffer (20 mM Tris-HCl, 5 mM EDTA, pH 7.7). Large particles and debris were cleared by low speed centrifugation (200xg, 20 min, 4° C.). Membranes were collected from the supernatant fraction by high speed centrifugation (32,000xg, 18 min, 4° C.) washed with ice-cold hypotonic buffer, and Collected again by high speed centrifugation (32,000xg, 18 min, 4 ° C). The final membrane pellet was resuspended by sonication into a small volume (~500 μl) of ice-cold binding buffer (10 mM NaCl, 20 mM HEPES, 0.22 mM $KH_2PO_4$, 1.26 mM $CaCl_2$, 0.81 mM $MgSO_4$, pH 7.4). Protein concentration was measured by the Bradford method (19) using Bio-Rad Reagent, with bovine serum albumin as a standard.

Radioligand Binding to Membrane Suspensions

Membrane suspensions were diluted in binding buffer supplemented with 0.1% bovine serum albumin and 0.1% bacitracin to yield an optimal membrane protein concentration: ~0.02 mg/ml for human Y1 receptors, ~0.003 mg/ml for CG-13 receptors, and ~0.25 mg/ml for SK-N-Be(2) (under these conditions, $^{125}$I-PYY bound by membranes in the assay was less than 10% of $^{125}$I-PYY delivered to the sample). $^{125}$I-PYY and non-labeled peptide competitors were also diluted to desired concentrations in supplemented binding buffer. Individual samples were then prepared in 96-well polypropylene microtiter plates by mixing membrane suspensions (200 ul), $^{125}$I-PYY (25 ul), and non-labeled peptides or supplemented binding buffer (25 ul). Samples were incubated in a 30° C. water bath with constant shaking for 120 min. Incubations were terminated by filtration over Whatman GF/C filters (pre-coated with 0.5% polyethyleneimine and air-dried before use). Filter-trapped membranes were counted for $^{125}I$ in a gamma counter. Non-specific binding was defined by 100 nM human NPY. Specific binding in time course and competition studies was typically 80%; most non-specific binding was associated with the filter. Binding data were analyzed using nonlinear regression and statistical techniques available in the GraphPAD InPlot package (San Diego, Calif.).

Creation of a Stably Expressing Cell Line pcEXV-hY2 DNA was transfected into the 293 human embryonic kidney cell line by the calcium phosphate transfection method. The 293 cells were grown in minimal essential medium (MEM) with Hank's salts, plus 2 mM glutamine, 100 international units of penicillin, streptomycin at 100 ug/ml, and 10% fetal calf serum, in 5% $CO_2$ at 37° C. Stably transfected cells were selected for two weeks in media containing G-148 (1 mg/ml) and screened for the ability to bind $^{125}I$-PYY. Several clones were selected based on preliminary measurements of cell density. One positive clone, designated 293 -hY2-10, was chosen for further characterization in binding and functional assays. This clone displayed saturable binding of $^{125}I$-porcine PYY in membrane preparations: $B_{max}$=200 fmol/mg membrane protein, $K_d$=5 pM, (n=1). When incubated with various concentrations of human PYY, it elicited a concentration-dependent inhibition of forskolin-stimulated cAMP accumulation as determined by radioimmunoassay. Clone 293-hY2-10 also elicited a concentration-dependent increase in free intracellular calcium as determined by Fura-2 florescence. The calcium response, which probably reflects mobilization of intracellular calcium stores, was inhibited by pretreatment of cells with pertussis toxin. $EC_{50}$ values for both the cAMP and the calcium response are currently under investigation.

Reagents

Cell culture media and supplements were from Specialty Media (Lavallette, N.J.). Cell culture plates (150 mm) were from Corning (Corning, N.Y.). Cell culture flasks (225 $cm^2$) and polypropylene microtiter plates were from Co-star (Cambridge, Mass.). Porcine $^{125}I$-PYY was from New England Nuclear (Boston, Mass.). NPY and related peptide analogs were from either Bachem California (Torrance, Calif.) or Peninsula (Belmont, Calif.). Whatman GF/C filters were Brandel (Gaithersburg, Md.). Bio-Rad Reagent was from Bio-Rad (Hercules, Calif.). Bovine serum albumin and bacitracin were from Sigma (St. Louis. Mo.). All other materials were reagent grade.

RESULTS

In order to clone a human NPY receptor subtype (Y2), we used an expression cloning strategy in COS-7 cells (20, 21, 22). This strategy was chosen for its extreme sensitivity since it allows detection of a single "receptor positive" cell by direct microscopic autoradiography.

Since the Y2 receptor is described as a presynaptic receptor, it is difficult to locate cell bodies that actually contain this specific mRNA in restricted brain areas. We reasoned that human hippocampus was a good source of mRNA since it contains both a large number of interneurons and has been shown to carry a particularly dense population of Y2 receptors (23, 24, 25, 26). A human hippocampal cDNA library of $2.2\times10^6$ independent recombinants with a 3 kb average insert size was fractionated into 440 pools of ≈5000 independent clones. From the first 200 pools tested, three gave rise to positive cells in the screening assay (#145, 158 and 189). The last 220 pools tested were all negative.

Since both Y1 and Y2 receptor subtypes are expressed in the hippocampus (2), we analyzed the DNA of positive pools by PCR with Y1 specific primers. Pools #145 and #158 turned out to contain cDNAs encoding an Y1 receptor, but pool #189, negative by PCR (data not shown), likely contained a cDNA encoding a human hippocampal NPY receptor that was not Y1. Pool #189 was subdivided in 20 pools of 1000 clones each, and a preliminary pharmacological characterization was run on COS-7 cells transfected with DNA prepared from the secondary pools. This preliminary analysis revealed that a 100 fold excess of cold [$Leu^{31}$-$Pro^{34}$]NPY totally inhibited binding of $^{125}I$-PYY to control COS-7 cells transfected with the Y1 gene. In contrast, no significant inhibition of binding was observed when the same experiment was performed on COS-7 cells transfected with secondary pool #189-17 (data not shown). This is consistent with pool #189 containing a cDNA encoding a human hippocampal Y2 receptor. The sib selection was therefore pursued on pool #189 until a single clone was isolated (designated CG-13).

The isolated clone carries a 4.2 kb cDNA. This cDNA contains an open reading frame between nucleotides 1002 and 2147 that encodes a 381 amino acid protein (SEQ. I.D. No. 2). The unusually long 5'untranslated region could be involved in the regulation of translation efficiency or mRNA stability. The flanking sequence around the putative initiation codon conforms to the Kozak consensus sequence for optimal translation initiation (27, 28).

The hydrophobicity plot displayed seven hydrophobic, putative membrane spanning regions which makes the human hippocampal Y2 receptor a member of the G-protein coupled superfamily. The nucleotide and deduced amino acid sequences are shown in FIG. 1 and FIG. 2 respectively.

Like most G-protein coupled receptors, the Y2 receptor contains a consensus sequence for N-linked glycosylation, in the amino terminus (position 11) involved in the proper expression of membrane proteins (29). The Y2 receptor carries two highly conserved cysteine residues in the first two extracellular loops that are believed to form a disulfide bond stabilizing the functional protein structure (30). The Y2 receptor shows 7 potential phosphorylation sites for protein kinase C in positions 11, 27, 64, 145, 188, 250 and 340, 2 casein kinase sites in positions 174 and 358, and 2 cAMP- and cGMP-dependent protein kinase phosphorylation sites in positions 146 and 350. It should be noted that 7 of those 11 potential phosphorylation sites are located in intra-cellular loops 1, 2 and 3 as well as in the carboxy terminus of the receptor and therefore could play a role in regulating functional characteristics of the Y2 receptor (30). A potential palmitoylation site is present in the sequence at the cysteine found in position 326. A large number of G-protein coupled receptors carry a cysteine in the same position and O'Dowd et al. have speculated that it plays an important role in the functional coupling of the human $\beta_2$-adrenergic receptor (31). The formation of this additional cytosolic loop may influence the mobility of the receptor across the membrane (32).

When compared to the published human Y1 cDNA clone (10, 11) both at the nucleotide and overall amino acid level, the Y2 sequence shows surprisingly low homology, 48.1 and 31% respectively (FIGS. 3A–D and 4A–4B). The transmembrane domain identity of the human hippocampal Y2 receptor with other 7 TM receptors is shown on Table 1. The low TM identity with other G-protein coupled receptor families, with other peptide receptors and especially with the Y1 subtype raises the possibility that Y2 receptor subtypes belong to a new distinct sub-family of 7 TM peptide receptors. Conversely, NPY receptor subtypes could form a sub-family where members show unusually low levels of overall homology. It is interesting to observe that the mouse orphan receptor MUSGIR (mouse glucocorticoid induced receptor, 33) shows the highest TM identity (42%, Table 1) with our human Y2 receptor. The same comparison between human Y1 and Y2 TM regions only gives a score of 41% identity. If we were comparing the human Y2 receptor sequence with the human homolog of the MUSGIR receptor, the level of identity might even be higher. Therefore the MUSGIR receptor could be related to the NPY receptors and bind members of the pancreatic polypeptide ligand family. A full pharmacological evaluation of the human GIR homolog with NPY, PYY and PP related ligands is now underway to verify this hypothesis.

The Y2-like pharmacology of CG-13, originally identified by whole cell autoradiographic techniques, was further defined by membrane binding assays. The gene for the human hippocampal Y2 receptor was transiently expressed in COS-7 cells for full pharmacological evaluation. $^{125}$I-PYY bound specifically to membranes from COS-7 cells transiently transfected with the CG-13 construct. The time course of specific binding was measured in the presence of 0.06 nM $^{125}$I-PYY (FIG. 4–4B). The association curve was biphasic, with approximately 55% of the specific binding occurring during an initial rapid phase and 45% following a slower time course. For the rapid phase, the observed association constant ($K_{obs}$) was 1.28±0.02 $min^{-1}$ and $t_{1/2}$ was 0.5 min; equilibrium binding was 95% complete within 2 min and 100% complete within 5 min (n=3). For the slow phase, $K_{obs}$ was 0.02±0.00 $min^{-1}$ and $t_{1/2}$ was 37 min; equilibrium binding was 90% complete within 120 min, 95% complete within 160 min and 100% complete within 280 min (n=3). Total equilibrium binding, composed of both phases, was 95% complete within 120 min and 100% complete within 240 min. The biphasic association curve may reflect a complex pattern of receptor surface binding followed by access to deep-seated binding sites, as has been suggested by Schwartz and co-workers for Y2 receptors (34). For comparison, we also measured the time course of binding to human Y1 receptors transiently expressed in COS-7 cells. The association curve was monophasic, with a $K_{obs}$ of 0.06±0.02 $min^{-1}$ and a $t_{1/2}$ of 12 min; equilibrium binding was 95% complete within 51 min and 100% complete within 90 min (n=3). The different patterns of association for CG-13 and human Y1 receptors suggest novel mechanisms of receptor/ligand interaction.

Saturation binding data for $^{125}$I-PYY were fit to a one-site model with an apparent $K_d$ of 0.069±0.009 nM and an apparent $B_{max}$ of 7.8±0.4 pmol/mg membrane protein, corresponding to approximately 7.5×$10^5$ receptors/cell (n=3; FIG. 2). Given that the transfection efficiency was 20–30% (data not shown), the receptor density on transfected cells was probably closer to 3×$10^6$/cell. Membranes from mock-transfected cells, when prepared and analyzed in the same way as those from CG-13-transfected cells, displayed no specific binding of $^{125}$I-PYY. We conclude that the $^{125}$I-PYY binding sites observed under the described conditions were derived from the CG-13 construct.

Figure 6:
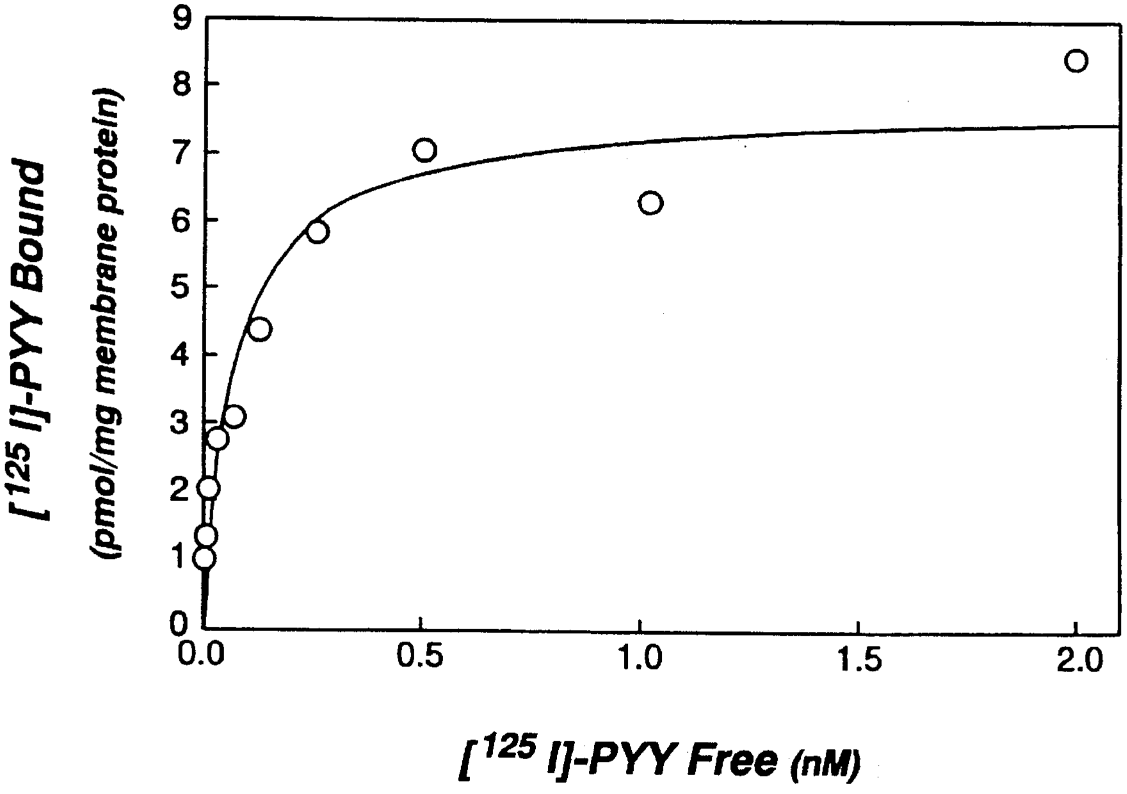
Figure 7A:
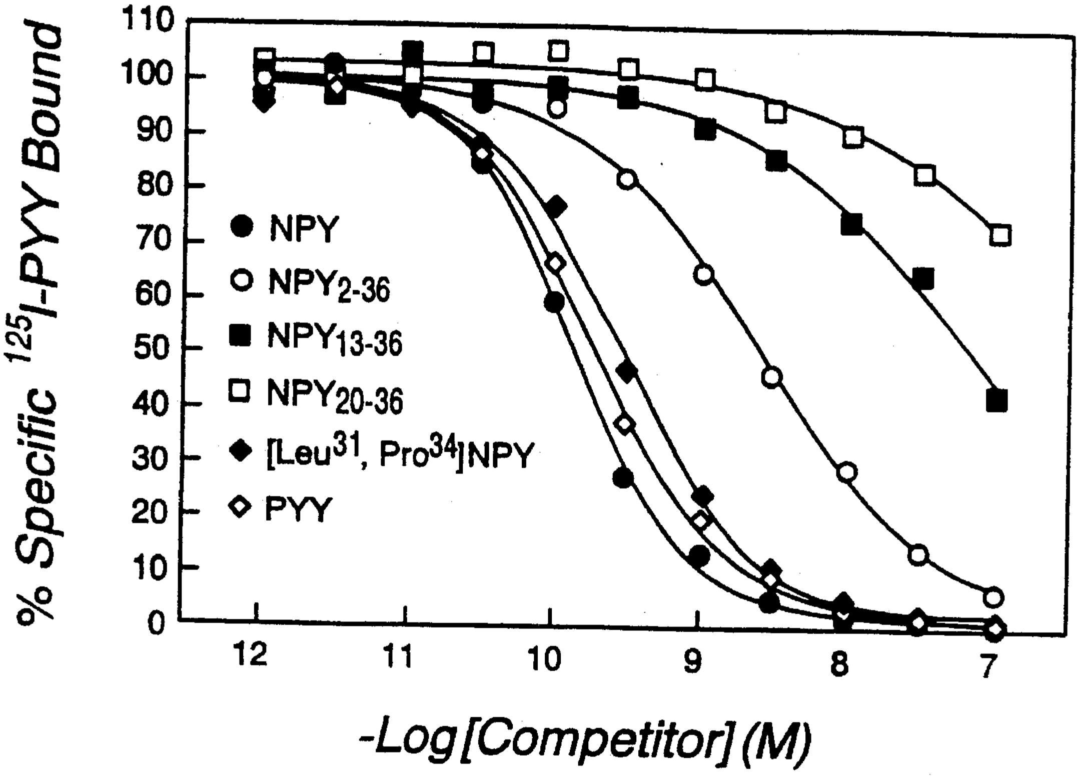
Figure 7B:
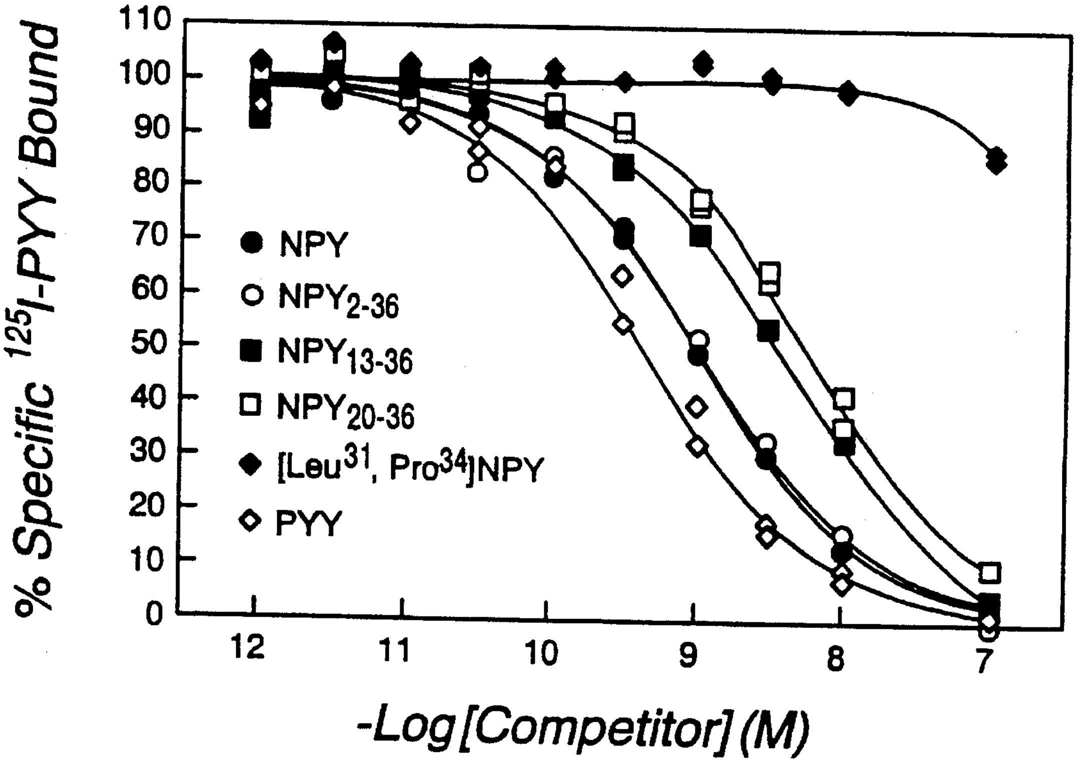

Y2 receptor recognition is thought to depend primarily upon the four C-terminal residues of NPY ($Arg^{33}$-$Gln^{34}$-$Arg^{35}$-$Tyr^{36}$-$NH_2$) preceded by an amphipathic α-helix (M4, M5); exchange of $Gln^{34}$ with $Pro^{34}$ is not well tolerated (4, 5). We therefore chose several C-terminal fragments and C-terminal modified peptides for competition binding studies. The rank order of affinity for selected compounds was derived from competitive displacement of $^{125}$I-PYY (FIG. 6 and Table 3). The CG-13 receptor was compared with two model systems: 1) the cloned human Y1 receptor (10, 11) transiently expressed in COS-7 cells, and 2) the Y2-like receptor population expressed by human SK-N-Be(2) neuroblastoma cells (2, 8). To our knowledge, no models for human Y3 and human PP receptors have been described.

CG-13 bound with high affinity to human NPY ($K_i$=0.69 nM) and even more so to human PYY ($K_i$=0.39 nM). The $K_i$ values are in agreement with numerous reports of pharmacologically defined Y2 receptors studied in NPY binding and functional assays (2). The opposite rank order was observed with human Y1 receptors, combined with stronger receptor/binding interactions ($K_i$=0.049 and 0.085 nM for human NPY and human PYY, respectively). It is interesting in this regard that CG-13 bound $^{125}$I-PYY ($K_d$=0.069 nM) with higher affinity than PYY ($K_i$=0.39 nM), suggesting that iodination may stabilize the receptor/ligand complex. The human Y1 receptor, in contrast, bound both $^{125}$I-PYY ($K_i$= 0.062+0.010 nM, n=3, data not shown) and PYY ($K_i$=0.085 nM) with comparable affinity. The fact that CG-13 and the human Y1 receptor bound NPY, PYY and $^{125}$I-PYY with different magnitudes and rank orders of affinity most likely reflects distinct mechanisms of peptide recognition which could potentially be exploited for the development of subtype-selective non-peptide ligands.

CG-13 also bound with high affinity to porcine NPY ($K_i$ =0.86 nM), which differs from human NPY by containing $Leu^{17}$ in the PP-fold rather than $Met^{17}$. CG-13 was relatively insensitive to N-terminal deletion of NPY and PYY; the affinity for porcine $NPY_{22-36}$ was only 5-fold less than that for full length porcine NPY. Extreme deletion of α-helical structure was less well tolerated; the affinity for porcine $NPY_{26-36}$ was 240-fold less than that for full length porcine NPY. Human [$Leu^{31}$,$Pro^{34}$]NPY and human PP, both having $Pro^{34}$ rather than $Glu^{34}$, did not bind well ($K_i$>300 nM) Hydrolysis of the carboxy terminal amide to free carboxylic acid, as in NPY free acid, also disrupted binding affinity for CG-13 ($K_i$>300 nM). The terminal amide appears to be a common structural requirement for pancreatic polypeptide family/receptor interactions.

The competitive displacement data indicate that CG-13 binds PYY with equal or greater affinity than NPY. The C-terminal region of NPY is the primary pharmacophore. CG-13 does not tolerate exchange of $Gln^{34}$ with $Pro^{34}$, as revealed by low affinity interactions with human [$Leu^{31}$, $Pro^{34}$]NPY and human PP. The binding profile, which is shared by SK-N-Be(2) cell receptors but not by human Y1 receptors, is characteristic of the pharmacologically defined Y2 receptor (2, 8; see also Table 2). The membrane binding studies therefore confirm and extend our assessment that CG-13 encodes a human Y2 receptor.

DISCUSSION

Attempts to isolate new NPY receptor subtypes based on sequence homology with the Y1 receptor have not been successful so far. Therefore, we choose an expression cloning approach where a functional receptor is actually detected with exquisite sensitivity on the surface of transfected cells, using a highly specific iodinated ligand. Using this strategy, we have identified a human cDNA encoding the pharmacologically defined Y2 receptor. The fact that we had to screen $2.2\times10^6$ independent clones with a 3 kb average insert size to find one clone reveals either a very strong bias against Y2 cDNA cloning in the cDNA library construction procedure or the Y2 mRNA is expressed at very low levels in human hippocampal tissue. The longest reading frame in the cDNA encodes a 381 amino acid protein with an estimated molecular weight of 42 kD. Given the fact that there is an N-linked glycosylation site in the amino terminus, the apparent molecular weight could be slightly higher and in good agreement with published data on the molecular weight of the human hippocampal Y2 receptor at 50 kD (36). The Y2 receptor carries a large number of potential phosphorylation sites which could be involved in the regulation of its functional characteristics.

The nucleotide and amino acid sequence analysis both reveal low identity levels with all 7 TM receptors including the human Y1 receptor. The highest transmembrane amino acid identity is found with the mouse MUSGIR receptor. A pharmacological profile on the human GIR homolog will be established with NPY, PYY and pancreatic polypeptide related ligands to find out if this orphan receptor belongs to the same pharmacologically defined neuropeptide Y receptor sub-family. The human Y2 receptor shares very low amino acid identity with the previously cloned human Y1 receptor (31% overall and 41% in transmembrane regions). CG-13 also displays a unique pharmacological profile and a unique time course of association with $^{125}$I-PYY. The dramatic differences in sequence and pharmacological profile between the human Y1 and Y2 receptors suggest that they might be encoded by two unrelated genes whose products have evolved into binding the same family of ligands. Conversely, they could have diverged from a common ancestor very early in evolution and undergone multiple mutations leading to distinct pharmacological characteristics.

The cloning of the human hippocampal Y2 receptor represents a novel starting point for the development of receptor subtype-selective agonists and antagonists. As NPY and its receptors are widely distributed throughout the human body (1, 2), the availability of the Y2 receptor clone will help in the understanding of NPY physiology, pathophysiology, and the therapeutic treatment of disease.

CG-13 exhibits features of a model Y2 receptor, including 1) binding affinity for PYY equal to or greater than that for NPY, 2) relative insensitivity to N-terminal deletion of NPY, and 3) low tolerance for modification of $Gln^{34}$ in NPY and NPY-like peptides (M3; see also Table 1). Our data do not support classification of CG-13 as a Y1 receptor, in which case it would tolerate exchange of $Pro^{34}$ for $Gln^{34}$ but not N-terminal deletion of NPY (3, 4, 5, 8, 10,11). Neither do the data support classification of CG-13 as a Y3 receptor, in which case it would display greater affinity for NPY than for PYY (M9). Finally, the data do not support classification of CG-13 as a PP receptor, in which case it would display greater affinity for PP than for NPY or PYY (3, 9). The binding profile is consistent with its having been cloned from hippocampus, a well-established model for Y2 receptors (35, 36, 37). As pharmacological evidence accumulates for potentially novel receptor subtypes such as the "atypical YI" receptor proposed to regulate feeding behavior (38), we can further evaluate the identity of CG-13. The strongest data at this time supports the classification of CG-13 as a Y2 receptor.

CG-13 represents the first receptor to be cloned from a subtype family other than Y1. The reported Y3 receptor cloned from bovine brain (39) was later described as having been misidentified (41, 42). A Y2-like receptor (PR4) was cloned from drosophila and characterized using mammalian analogs of NPY (40). The classification of this receptor is controversial, however. The receptor was relatively insensitive to NPY; concentrations ranging from 0.3 to 10 μM were required to elicit calcium mobilization in oocytes injected with PR4 mRNA (40). The receptor also displayed a rank order of potency for NPY analogs distinct from that observed in mammalian systems (1, 40). Furthermore, an NPY analog has not been isolated from drosophila (1). It is possible that an unidentified ligand in drosophila can activate PR4 more readily than NPY, and as such, the receptor may eventually be reclassified.

A number of studies have indicated that NPY receptors are coupled to G proteins (8, 43, 44, 45). Inhibition of cAMP and $Ca^+$ mobilization has been proposed as a common dual coupling mechanism of NPY/PYY receptors. Both phenomena however do not necessarily coexist in all tissues or cell lines tested (8). Moreover, there are conflicting reports in the literature whether the inhibition of adenylate cyclase induced by the Y2 receptor is pertussis toxin sensitive or not (2). Cloning of a human Y2 receptor subtype will allow us to clarify those issues by establishing various stably transfected cell lines and performing functional studies.

The expression cloning of a human Y2 receptor allows, for the first time, the ability to develop subtype specific drugs and represents a major advance in our ability to analyze NPY-mediated physiological processes. Pharmacologically defined Y2 receptors have a widespread anatomical distribution (2). They represent the predominant NPY receptor in brain, with the highest density in hippocampus and relatively high expression in almost all other areas including olfactory bulb, basal ganglia, amygdaloid complex, thalamic and hypothalamic nuclei, pituitary, pineal gland, cerebellum, and brainstem. Peripheral localization includes sympathetic neurons, dorsal root ganglia, stomach chief cells, intestinal enterocytes, kidney proximal tubule, trachea, and vascular smooth muscle. Y2 receptors are therefore in a position to potentially regulate a variety of physiological functions including cognitive enhancement, circadian rhythm, EEG synchronization, body temperature, blood pressure, locomotor activity, neuroendocrine release, sympathetic activation, sensory transmission, gastrointestinal function, intestinal secretion, renal absorption, and cardiovascular function (1, 2).

Y2 receptors are attractive targets for drug design (1). Y2 receptor regulation may be useful in the treatment of several pathophysiological conditions including memory loss, epileptic seizure, pain, depression, hypertension, locomotor problems, sleep disturbances, eating disorders, sexual/reproductive disorders, nasal congestion, and diarrhea (1, 2). A rigorous investigation of Y2-related pathophysiology has been hindered by the absence of suitable non-peptide ligands. The chemical synthesis of subtype selective agonists and antagonists as potential drug candidates will be greatly accelerated by preliminary screening against a homogeneous population of cloned human Y2 receptors. As more specific pharmacological tools become available for probing receptor function, additional therapeutic indications are likely to be discovered.

We do not know whether CG-13 accounts for all of the pharmacological Y2 receptors so far described, or whether the Y2 receptor population is further divided into distinct receptor subtypes. Indeed, there is some suggestion of receptor heterogeneity within the Y2 receptor population (2). These are issues which can now be resolved using nucleotide sequence from CG-13 as the basis for in situ localization, anti-sense strategies, homology cloning, and related techniques. Such approaches will enable us to investigate the existence of potentially novel NPY receptor subtypes, in humans and other species, with pharmacologic and therapeutic significance.

TABLE 1

% aminoacid TM identity of the NPY-2 receptor with other 7 TM Receptors

| | | | | | |
|---|---|---|---|---|---|
| m MUSGIR | 42 | h NPY-1 | 41 | | |
| h 5HT1A | 28 | h Adenosine A2b | 28 | h Substance K | 33 |
| h 5HT2 | 31 | h Adenosine A1 | 29 | h Substance P | 32 |
| h alpha-Adrenergic-1b | 34 | h Dopamine D1 | 31 | h Neurokinin-3 | 33 |
| h alpha-Adrenergic-2a | 34 | h Dopamine D2 | 32 | h Interleukin-8 | 33 |
| h beta-Adrenergic-1 | 35 | bov Hist H1 | 25 | h $Angiotensin_1$ | 33 |
| | | h Hist H2 | 28 | h $Angiotensin_2$ | 27 |
| | | | | m Thyrotropin releasing hormone | 27 |
| | | | | h Bradykinin | 25 |
| | | | | r mas oncogene | 20 |

TABLE 2

Pharmacologically defined receptors for NPY and related pancreatic polypeptides. Rank orders of affinity are based on published reports of binding and functional data (M9, M24, M3, M10). Missing peptides in the series reflect a lack of published information.

| | Affinity (-p$K_i$ or -p$EC_{50}$) | | | | | |
|---|---|---|---|---|---|---|
| Receptor | 11 to 10 | 10 to 9 | 9 to 8 | 8 to 7 | 7 to 6 | <6 |
| Y1 | NPY<br>PYY<br>[$Leu^{31}$,$Pro^{34}$]NPY | | $NPY_{2-36}$ | $NPY_{13-36}$ | PP | |
| Y2 | | PYY<br>NPY<br>$NPY_{2-36}$ | $NPY_{13-36}$ | | | [$Leu^{31}$,$Pro^{34}$]NPY<br>PP |
| Y3 | | NPY | [$Pro^{34}$]NPY | $NPY_{13-36}$<br>PP | | PYY |
| PP | PP | | [$Leu^{31}$,$Pro^{34}$]NPY | | | NPY |

TABLE 3

Pharmacological profile of the CG-13 receptor. Binding data reflect competitive displacement of $^{125}$I-PYY from membranes of COS-7 cells transiently expressing CG-13 receptors. Peptides were tested at concentrations ranging from 0.001 nM to 100 nM. $IC_{50}$ values corresponding to 50% displacement were determined by nonlinear regression analysis and converted to $K_i$ values according to the equation, $K_i = IC_{50}/(1 + [L]/K_d)$, where [L] is the $^{125}$I-PYY concentration and $K_d$ is the equilibrium dissociation constant of $^{125}$I-PYY. The data shown are representative of at least two independent experiments.

| Competitor | Human Y1, $K_i$ (nM) | CG-13, $K_i$ (nM) | SK-N-Be(2), $K_i$ (nM) |
|---|---|---|---|
| human PYY | 0.085 ± 0.021 | 0.39 ± 0.05 | 0.11 ± 0.02 |
| human NPY | 0.049 ± 0.009 | 0.69 ± 0.14 | 0.13 ± 0.02 |
| porcine $NPY_{2-36}$ | 1.4 ± 0.2 | 0.78 ± 0.13 | 0.41 ± 0.09 |
| porcine NPY | 0.049 ± 0.001 | 0.86 ± 0.13 | 0.28 ± 0.04 |
| porcine $PYY_{13-36}$ | 32 ± 7 | 1.5 ± 0.2 | 0.86 ± 0.14 |
| porcine $NPY_{18-36}$ | 28 ± 5 | 1.5 ± 0.2 | 2.1 ± 0.5 |
| porcine $NPY_{13-36}$ | 51 ± 16 | 2.4 ± 0.4 | 1.8 ± 0.4 |
| porcine $NPY_{20-36}$ | 62 ± 6 | 3.4 ± 0.3 | 3.1 ± 0.6 |
| porcine $NPY_{16-36}$ | 45 ± 4 | 3.8 ± 0.7 | 5.0 ± 0.5 |
| porcine $NPY_{22-36}$ | 170 ± 30 | 4.6 ± 0.1 | 3.2 ± 0.6 |
| porcine $NPY_{26-36}$ | >300 | 210 ± 60 | 70 ± 7 |
| human NPY free acid | >300 | >300 | 280 ± 120 |

TABLE 3-continued

Pharmacological profile of the CG-13 receptor. Binding data reflect competitive displacement of $^{125}$I-PYY from membranes of COS-7 cells transiently expressing CG-13 receptors. Peptides were tested at concentrations ranging from 0.001 nM to 100 nM. $IC_{50}$ values corresponding to 50% displacement were determined by nonlinear regression analysis and converted to $K_i$ values according to the equation, $K_i = IC_{50}/(1 + [L]/K_d)$, where [L] is the $^{125}$I-PYY concentration and $K_d$ is the equilibrium dissociation constant of $^{125}$I-PYY. The data shown are representative of at least two independent experiments.

| Competitor | Human Y1, $K_i$ (nM) | CG-13, $K_i$ (nM) | SK-N-Be(2), $K_i$ (nM) |
|---|---|---|---|
| human PP | 200 ± 70 | >300 | >300 |
| human [$Leu^{31}$,$Pro^{34}$]NPY | 0.13 ± 0.02 | >300 | >300 |

REFERENCES

1. Wahlestedt, C., and D. J. Reis. (1993). Neuropeptide Y-Related Peptides and Their Receptors—Are the Receptors Potential Therapeutic Targets? Ann. Rev. Pharmacol. Tox., 32, 309–352.
2. Dumont, Y., J. C. Martel, A. Fournier, S. St-Pierre, and R. Quirion. (1992). Neuropeptide Y and neuropeptide Y receptor subtypes in brain and peripheral tissues. Progresss in Neurobiology, 38, 125–167.
3. Schwartz, T. W., J. Fuhlendorff, L. L. Kjems, M. S. Kristensen, M. Vervelde, M. O'Hare, J. L. Krstenansky, and B. Bjornholm. (1990). Signal epitopes in the three-dimensional structure of neuropeptide Y. Ann. N.Y. Acad. Sci., 611, 35–47.
4. Fuhlendorff, J., U. Gether, L. Aakerlund, N. Langeland-Johansen, H. Thogersen, S. G. Melberg, U. B. Olsen, O. Thastrup, and T. W. Schwartz. (1990). [$Leu^{31}$,$Pro^{34}$] Neuropeptide Y: A specific $Y_1$ receptor agonist. Proc. Natl. Acad. Sci. USA, 87, 182–186.
5. Grundemar, L., J. L. Krstenansky, and R. Hakanson. (1992). Activation of neuropeptide Y1 and neuropeptide Y2 receptors by substituted and truncated neuropeptide Y analogs: identification of signal epitopes. Eur. J. Pharmacol., 232, 271–278.
6. Beck, A. G., G. Jung, W. Gaida, H. Koppen, R. Lang, and G. Schnorrenberg. (1989). Highly potent and small neuropeptide Y agonist obtained by linking $NPY_{1-4}$ via a spacer to alphahelical $NPY_{25-36}$. FEBS Lett., 244, 119–122.

7. Beck-Sickinger, A. G., W. Gaida, G. Schnorrenberg, R. Lang, and G. Jung. (1990). Neuropeptide Y: Identification of the binding site. Int. J. Peptide Protein Res., 36, 522–530.
8. Wahlestedt, C., Regunathan, S., and D. J. Reis. (1991). Identification of cultured cells selectively expressing Y1-, Y2-, or Y3-type receptors for neuropeptide Y/peptide YY. Life Sciences, 50, PL-7–PL-12.
9. Schwartz, T. W., S. P. Sheikh, and M. M. T. O'Hare. (1987). Receptors on phaeochromocytoma cells for two members of the PP-fold family-NPY and PYY. FEBS Lett., 255, 209–214
10. Larhammar, D., A. G. Blomqvist, F. Yee, E. Jazin, H. Yoo, and C. Wahlestedt. (1992). Cloning and functional expression of a human neuropeptide Y/peptide YY receptor of the Y1 type. J. Biol. Chem., 267, 10935–10938.
11. Herzog, H., Y. J. Hort, H. J. Ball, G. Hayes, J. Shine, and L. Selbie. (1992). Cloned human neuropeptide Y receptor couples to two different second messenger systems. Proc. Natl. Acad. Sci. USA, 89, 5794–5798.
12. Eva, C., Keinanen, K., Monyer, H., Seeburg, P., and Sprengel, R. (1990). Molecular cloning of a novel G protein-coupled receptor that may belong to the neuropeptide receptor family. FEBS Lett., 271, 80–84.
13. Chirgwin, J. M., A. E. Przybyla, R. J. MacDonald, and W. J. Rutter. (1979). Isolation of biologically active ribonucleic acid from sources enriched in ribonuclease. Biochemistry, 18, 5294–5299.
14. Gubler, U abd B. J. Hoffman. (1983). A simple and very efficient method for generating cDNA libraries. Gene, 25, 263–269
15. Aruffo, A. and Seed, B. (1987). Molecular cloning of a CD28 cDNA by a high efficiency COS Cell expression system. Proc. Natl. Acad. Sci. USA, 84, 8573–8577.
16. Sambrook, J., Fritsch, E. F. and Maniatis, T. (1989). Molecular cloning: a laboratory manual (Cold Spring Harbor Laboratory Press, Cold Spring Harbor, N.Y.), 2nd Ed.
17. Warden, D. and H. V. Thorne. (1968). Infectivity of polyoma virus DNA for mouse embryo cells in presence of diethylaminoethyl-dextran. J. Gen. Virol., 3, 371.
18. Mc Cormick, M. (1987). Sib Selection. Methods in Enzymology, 151, 445–449.
19. Bradford, M. M. (1976). A rapid and sensitive method for the quantitation of microgram quantities of protein utilizing the principle of protein-dye binding. Anal. Biochem., 72,248–254.
20. Gearing, D. P., King, J. A., Gough, N. M. and Nicola N. A. (1989). Expression cloning of a receptor for human granulocyte-macrophage colony-stimulating factor. EMBO J., 8, 3667–3676.
21. Kluxen, F. W., Bruns, C. and Lubbert H. (1992). Expression cloning of a rat brain somatostatin receptor cDNA. Proc. Natl. Acad. Sci., 89, 4618–4622.
22. Kieffer, B., Befort, K., Gaveriaux-Ruff, C. and Hirth, C. G. (1992). The δ-opioid receptor: Isolation of a cDNA by expression cloning and pharmacological characterization. Proc. Natl. Acad. Sci., 89, 12048–12052.
23. Dumont, Y., A. Fournier, S. St.-Pierre, Schwartz, T. W. and R. Quirion. (1990). Differential distribution of neuropeptide Y1 and Y2 receptors in the rat brain. Eur. J. Pharmacol., 191, 501–503.
24. Aicher, S. A., Springston, M., Berger, S. B., Reis, D. J and Wahlestedt, C. (1991). Receptor selective analogs demonstrate NPY/PYY receptor heterogeneity in rat brain. Neurosci. lett., 130, 32–36.
25. Wei Li and T. D. Hexum. (1991). Characterization of neuropeptide Y (NPY) receptors in human hippocampus. Brain Research., 553, 167–170.
26. Bayer, S. A. (1985). Hippocampal Region, in The rat nervous system, Vol. I, p335–352. (Acad. Press, George Paxinos Ed.).
27. Kozak, M. (1989). The scanning model for translation: an update. J. Cell Biol. 108, 229–241.
28. Kozak, M. (1991). Structural features in eukaryotic mRNAs that modulate the initiation of translation. J. Biol. Chem., 266, 19867–19870.
29. Kornfeld, R. and Kornfeld, S. (1985). Assembly of asparagine linked oligosaccharides. Annu. Rev. Biochem., 54, 631–664.
30. Probst, W. C., Snyder, L. A., Schuster, D. I., Brosius, J and Sealfon, S. C. (1992). Sequence alignment of the G-protein coupled receptor superfamily. DNA and Cell Bio., 11, 1–20.
31. O'Dowd, B. F., M. Hantowich, M. G. Caron, R. J. Lefkowitz and M. Bouvier. Palmitoylation of the human $\beta_2$-adrenergic receptor. J. B. C., 264, 7564–7569 (1989).
32. Findlay, J. and Eliopoulos, E. (1990). Three dimensional modelling of G protein-linked receptors. Science, 11, 492–499.
33. Harrigan, M. T., Faith Campbell N. and Bourgeois S. (1991). Identification of a gene induced by glucocorticoids in murine T-cells: A potential G protein-coupled receptor. Molecular Endocrinology, 5, 1331–1338.
34. Fuhlendorff, J., A. G. Beck-Sickinger, A. Holm, M. Barfoed, K. Borch, H. Lund, B. Lundt, N. L. Johansen, H. Thogersen, and T. W. Schwartz.(1993). Membrane association of NPY—a prerequisite for receptor binding. Neuropeptide Y Conference Abstracts, Cambridge. B40.
35. Sheikh, S. P., M. M. T. O'Hare, O. Tortora, and T. W. Schwartz. (1989). Binding of monoiodinated neuropeptide Y to hippocampal membranes and human neuroblastoma cell lines. J. Biol. Chem., 264, 6648–6654.
36. Li, W. and T. D. Hexum. (1991). Characterization of neuropeptide Y (NPY) receptors in human hippocampus. Brain Research, 553, 167–170.
37. Colmers, W. F., G. J. Klapstein, A. Fournier, S. St-Pierre, and K. A. Treherne. (1991). Presynaptic inhibition by neuropeptide Y in rat hippocampal slice in vitro is mediated by a Y2 receptor. Br. J. Pharmacol., 102, 41–44.
38. Stanley, B. G., W. Magdalin, A. Seirafi, M. M. Nguyen, and S. F. Leibowitz. (1992). Evidence for neuropeptide Y mediation of eating produced by food deprivation and for a variant of the $Y_1$ receptor mediating this peptide's effect. Peptides, 13, 581–587.
39. Rimland, J., W. Xin, P. Sweetnam, K. Saijoh, E. J. Nestler, and R. S. Duman. (1991). Sequence and expression of a neuropeptide Y receptor cDNA. Mol. Pharmacol., 40, 869–875.

40. Li, X.-J., Y.-N. Wu, R. A. North, and M. Forte. (1992). Cloning, functional expression, and developmental regulation of a neuropeptide Y receptor from *drosophila melanogaster.* J. Biol. Chem., 267, 9–12.

41. Jazin, E. E., Yoo, H., Blomqvist, A. G., Yee, F., Weng, G., Walker, M. W., Salon, J., Larhammar, D., and Wahlestedt, C. (1993). A proposed bovine neuropeptide Y (NPY) receptor cDNA clone, or its human homologue, confers neither NPY binding sites nor NPY responsiveness on transfected cells. Reg. Peptides, 47, 247–258.

42. Herzog, H., Y. J. Hort, J. Shine, and L. A. Selbie. (1993). Molecular cloning, characterization, and localization of the human homolog to the reported bovine NPY Y3 receptor: lack of NPY binding and activation. DNA and Cell Biology, 12, 465–471.

43. Wahlestedt, C., Grundemar, L., Hakanson, R., Heilig, M., Shen, G. H., Zukowska-grojec, Z. and Reis, D. J. (1990). Neuropeptide Y receptor subtypes, Y1 and Y2. Ann. NY Acad. Sci., 611, 7–26.

44. Unden, A. and Bartfai, T. (1984). Regulation of neuropeptide Y (NPY) binding by guanine nucleotide in rat cerebral cortex. FEBS Lett., 177, 125–128.

45. Michel, M. C. (1991). Receptors for neuropeptide Y: multiple subtypes and multiple second messengers. Trends Pharmacol. Sci., 12, 389–394.

46. De Wied, D. In: Neuropeptides: Basics and Perspectives (Elsevier, Amsterdam-New York-Oxford), 1990.

47. Heilig, M. and E. Widerlov. Neuropeptide Y: an overview of central distribution, functional aspects, and possible involvement of neuropsychiatric illnesses. Acta Psychiatr. Scand., 82, 95–114 (1990).

48. Lundberg, J. M., A. Hemsen, O. Larsson, A. Rudehill, A. Saria, and B. Fredholm. Neuropeptide Y receptor in pig spleen: binding characteristics, reduction of cyclic AMP formation and calcium antagonist inhibition of vasoconstriction. Eur. J. Pharmacol., 145, 21–29 (1988).

49. Hinson, J., C. Rauh, and J. Coupet. Neuropeptide Y stimulates inositol phospholipid hydrolysis in rat brain microprisms. Brain Res., 446, 379–382 (1988).

50. Mihara, S., Y. Shigeri, and M. Fujimoto. Neuropeptide Y-induced intracellular $Ca^{2+}$ increase in vascular smooth muscle cells. FEBS Lett., 259, 79–82 (1989).

51. Aakerlund, L., U. Gether, J. Fuhlendorff, T. W. Schwartz, and O. Thastrup. Y1 receptors for neuropeptide Y are coupled to mobilization of intracellular calcium and inhibition of adenylate cyclase. FEBS Lett., 260, 73–78 (1990).

52. Eva, C., A. Oberto, R. Sprengel, and E. Genazzani. The murine NPY-1 receptor gene: structure and delineation of tissue specific expression. FEBS Lett., 314, 285–288 (1992).

53. Wahlestedt, C., N. Yanaihara, and R. Hakanson. Evidence for different pre- and post-junctional receptors for neuropeptide Y and related peptides. Regul. Pept., 13, 307–318 (1986).

54. Bottcher, G., K. Sjolund, E. Ekblad, R. Hakanson, T. W. Schwartz, and F. Sundler. Co-existence of peptide YY in glicentin immunoreactivity in endocrine cells of the gut. Regul. Pept., 8, 261–273 (1984).

55. Laburthe, M., B. Chenut, C. Rouyer-Fessard, K. Tatemoto, A. Couvineau, A. Servin, and B. Amiranoff. Interaction of peptide YY with rat intestinal epithelial plasma membranes: binding of the radioiodinated peptide. Endocrinology, 118, 1910–1917 (1986).

56. Laburthe, M. Peptide YY and neuropeptide Y in the gut: Availability, biological actions, and receptors. Trends Endocrinol. Metab., 1, 168–174 (1990).

57. Voisin, T., M. Bens, F. Cluzeaud, A. Vandewalle, and M. Laburthe. Peptide YY receptors in the proximal tubule PKSV-PCT cell line derived from transgenic mice: relation with cell growth. J. Biol. Chem., 268, 20547–20554 (1993).

58. McDermott, B. J., Millar, B. B., and Piper, H. M. Cardiovascular effects of neuropeptide Y: receptor interactions and cellular mechanisms. Cardiovascular Research, 27, 893–905 (1993).

59. Westfall, T. C., Han, S. P., Kneupfer, M., Martin, J., Chen, X., Del Valle, Ciarleglio, A., and Nass, L. (1990). Neuropeptides in Hypertension: Role of Neuropeptide Y and Calcitonin Gene Related Peptide. Brit. J. Clin. Pharmacol., 30, 755–825 (1990).

60. Tsuda, K., Tsuda, S., Goldstein. M., and Masauyama, Y. Effects of Neuropeptide Y on Norepinephrine Release in Hypothtalmic Slices of Spontaneously Hypertensive Rats. Eur. J. Pharmacol., 182, 175–179 (1990).

61. Friel, D. D., Miller, R. J., an Walker, M. W. Neuropeptide Y: a powerful modulator of epithelial ion transport. Brit. J. Pharmacol., 88, 425–431 (1986).

62. Playford, R. J., Domin, J., Beecham, J., Parmark, K. I., Tatemoto, K., Bloom, S. R., and Calam, J. Peptide YY: A natural defense against diarrhoea. Lancet, 335, 1555–1557 (1990).

63. Colmers, W. F., Klapstein, G. J., Fournier, A., St-Pierre, S., and Treherne, K. A. Presynaptic Inhibition by neuropeptide Y in rat hippocampal slice in vitro is mediated by a Y2 receptor. Brit. J. Pharmacol., 102, 41–44 (1991).

64. Hua, X. Y., Boublik, J. H., Spicer, M. A., Rivier, J. E., Brown, M. R., and Yaksh, T. L. The antinociceptive effects of spinally administered Neuropeptide Y in the rat: systematic studies on structure-activity relationship. J. Pharmacol. Exp. Ther., 258, 243–253 (1991).

65. Calza, L., Giardino, L., Zanni, M., Velardo, A., Parchi, P., and Marrama, P. Daily changes of Neuropeptide Y-like immunoreactivity in the Suprachiamsmatic Nucleus of the rat. Regul. Pept., 27, 127–137 (1990).

66. Flood, J. F., Hernandez, E. N., and Morley, J. E. Modulation of memory processing by Neuropeptide Y. Brain Res., 421, 280–290 (1987).

67. Lacroix, J. S.; Auberson, S., Morel, D. R. Theodorsson, E., Hokfelt, T. and Lundberg, J. M. Vascular control of the pig nasal mucosa: distribution and effect of somatostatin in relation to noradrenaline and Neuropeptide Y. Regul. Pept., 40 (3), 373–87 (1992).

68. Modin, A., Pernow, J., and Lundberg, J. M. Evidence for two Neuropeptide Y receptors mediating vasoconstriction. Eur. J. Pharmacol. 203, 2, 165–171 (1991).

69. Lundberg, J. M., Franco-Cereceda, A., Lacroix, J. S., and Pernow, J. Neuropeptide Y and sympathetic neurotransmission. Ann. N.Y. Acad. Sci., 611, 166–174 (1990).

70. Lundberg, J. M. Peptidergic control of the autonomic regulation system in the orofacial region. Proc. Finn. Dent. Soc., 85, 4–5, 239–250 (1989).

71. Lacroix, J. S., Angg. ANG.ard, A., Hokfelt, T., O'Hare, M. M., Fahrenkrug, J. and Lundberg, J. M.

Neuropeptide Y: presence in sympathetic and parasympathetic innervation of the nasal mucosa. Dept. of Pharm., Karolinska Institutet, Stockholm (1993).

72. Rizzi, M., Monno, A., Samanin, R., Sperk, G., and Vezzani, A., Electrical kindling of the hippocampus in association with functional activation of Neuropeptide Y containing neurons. Euro. J. Neurosci., 5, 1534–1538 (1993).

73. Miller J. and Germain R. N., Efficient cell surface expression of class II MHC molecules in the absence of associated invariant chain, J. Exp. Med., 164, 1478 (1986).

74. J. S. Cohen, Trends in Pharm. Sci., 10, 435 (1989).

75. H. M. Weintraub, Sci. Am. January (1990) p. 40.

76. N. Sarver et al., Science, 247, 1222 (1990).

77. Low, M. J., Lechan, R. M., Hammer, R. E. et al. Science, 231, 1002–1004 (1986).

78. Oberdick, J., Smeyne, R. J., Mann, J. R., Jackson, S. and Morgan, J. I. Science, 248, 223–226 (1990).

79. Hogan B. et al. Manipulating the Mouse Embryo, A Laboratory Manual, Cold Spring Harbor Laboratory (1986).

80. Capecchi M. R. Science, 244, 1288–1292 (1989).

81. Zimmer, A. and Gruss, P. Nature, 338, 150–153 (1989).

---

What is claimed is:

1. An isolated nucleic acid molecule encoding a human Y2 receptor, wherein the human Y2 receptor has the amino acid sequence shown in FIG. 2 (Seq. I.D. No. 2).

2. An isolated nucleic acid molecule of claim 1, wherein the nucleic acid molecule is a DNA molecule.

3. An isolated DNA molecule of claim 2, wherein the DNA molecule is a cDNA molecule.

4. An isolated DNA molecule of claim 2, wherein the DNA molecule is a genomic DNA molecule.

5. An isolated nucleic acid molecule of claim 1, wherein the nucleic acid molecule is a RNA molecule.

6. A vector comprising the DNA molecule of claim 2.

7. A plasmid comprising the vector of claim 6.

8. A vector of claim 6 adapted for expression in a bacterial cell which comprises the regulatory elements necessary for expression of the DNA in the bacterial cell operatively linked to the DNA encoding the Y2 receptor as to permit expression thereof.

9. A vector of claim 6 adapted for expression in a yeast cell which comprises the regulatory elements necessary for expression of the DNA in the yeast cell operatively linked to the DNA encoding the Y2 receptor as to permit expression thereof.

10. A vector of claim 6 adapted for expression in an insect cell which comprises the regulatory elements necessary for expression of the DNA in the insect cell operatively linked to the DNA encoding the Y2 receptor as to permit expression thereof.

11. A vector of claim 6 adapted for expression in a mammalian cell which comprises the regulatory elements necessary for expression of the DNA in the mammalian cell operatively linked to the DNA encoding the Y2 receptor as to permit expression thereof.

12. A plasmid of claim 7 adapted for expression in a mammalian cell which comprises the regulatory elements necessary for expression of the DNA in the mammalian cell operatively linked to the DNA encoding the Y2 receptor as to permit expression thereof.

13. A plasmid designated pcEXV-hY2 (ATCC Accession No. 75659).

14. A mammalian cell comprising the plasmid of claim 7.

15. A mammalian cell of claim 14, wherein the mammalian cell is a COS-7 cell.

16. A mammalian cell of claim 14, wherein the mammalian cell is a 293 human embryonic kidney cell (ATCC Accession No. CRL 11537).

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 1280 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 43..1185

( x i ) SEQUENCE DESCRIPTION: SEQ ID NO:1:

```
GACTCTTGTG CTGGTTGCAG GCCAAGTGGA CCTGTACTGA AA ATG GGT CCA ATA      54
                                               Met Gly Pro Ile
                                                1

GGT GCA GAG GCT GAT GAG AAC CAG ACA GTG GAA GAA ATG AAG GTG GAA    102
Gly Ala Glu Ala Asp Glu Asn Gln Thr Val Glu Glu Met Lys Val Glu
  5                  10                  15                  20

CAA TAC GGG CCA CAA ACA ACT CCT AGA GGT GAA CTG GTC CCT GAC CCT    150
Gln Tyr Gly Pro Gln Thr Thr Pro Arg Gly Glu Leu Val Pro Asp Pro
                 25                  30                  35

GAG CCA GAG CTT ATA GAT AGT ACC AAG CTG ATT GAG GTA CAA GTT GTT    198
Glu Pro Glu Leu Ile Asp Ser Thr Lys Leu Ile Glu Val Gln Val Val
             40                  45                  50

CTC ATA TTG GCC TAC TGC TCC ATC ATC TTG CTT GGG GTA ATT GGC AAC    246
Leu Ile Leu Ala Tyr Cys Ser Ile Ile Leu Leu Gly Val Ile Gly Asn
         55                  60                  65

TCC TTG GTG ATC CAT GTG GTG ATC AAA TTC AAG AGC ATG CGC ACA GTA    294
Ser Leu Val Ile His Val Val Ile Lys Phe Lys Ser Met Arg Thr Val
     70                  75                  80

ACC AAC TTT TTC ATT GCC AAT CTG GCT GTG GCA GAT CTT TTG GTG AAC    342
Thr Asn Phe Phe Ile Ala Asn Leu Ala Val Ala Asp Leu Leu Val Asn
 85                  90                  95                 100

ACT CTG TGT CTA CCG TTC ACT CTT ACC TAT ACC TTA ATG GGG GAG TGG    390
Thr Leu Cys Leu Pro Phe Thr Leu Thr Tyr Thr Leu Met Gly Glu Trp
                105                 110                 115

AAA ATG GGT CCT GTC CTG TGC CAC CTG GTG CCC TAT GCC CAG GGC CTG    438
Lys Met Gly Pro Val Leu Cys His Leu Val Pro Tyr Ala Gln Gly Leu
            120                 125                 130

GCA GTA CAA GTA TCC ACA ATC ACC TTG ACA GTA ATT GCC CTG GAC CGG    486
Ala Val Gln Val Ser Thr Ile Thr Leu Thr Val Ile Ala Leu Asp Arg
        135                 140                 145
```

-continued

```
CAC   AGG   TGC   ATC   GTC   TAC   CAC   CTA   GAG   AGC   AAG   ATC   TCC   AAG   CGA   ATC        534
His   Arg   Cys   Ile   Val   Tyr   His   Leu   Glu   Ser   Lys   Ile   Ser   Lys   Arg   Ile
      150                           155                           160

AGC   TTC   CTG   ATT   ATT   GGC   TTG   GCC   TGG   GGC   ATC   AGT   GCC   CTG   CTG   GCA        582
Ser   Phe   Leu   Ile   Ile   Gly   Leu   Ala   Trp   Gly   Ile   Ser   Ala   Leu   Leu   Ala
165                           170                           175                           180

AGT   CCC   CTG   GCC   ATC   TTC   CGG   GAG   TAT   TCG   CTG   ATT   GAG   ATC   ATC   CCG        630
Ser   Pro   Leu   Ala   Ile   Phe   Arg   Glu   Tyr   Ser   Leu   Ile   Glu   Ile   Ile   Pro
                        185                           190                           195

GAC   TTT   GAG   ATT   GTG   GCC   TGT   ACT   GAA   AAG   TGG   CCT   GGC   GAG   GAG   AAG        678
Asp   Phe   Glu   Ile   Val   Ala   Cys   Thr   Glu   Lys   Trp   Pro   Gly   Glu   Glu   Lys
                  200                           205                           210

AGC   ATC   TAT   GGC   ACT   GTC   TAT   AGT   CTT   TCT   TCC   TTG   TTG   ATC   TTG   TAT        726
Ser   Ile   Tyr   Gly   Thr   Val   Tyr   Ser   Leu   Ser   Ser   Leu   Leu   Ile   Leu   Tyr
            215                           220                           225

GTT   TTG   CCT   CTG   GGC   ATT   ATA   TCA   TTT   TCC   TAC   ACT   CGC   ATT   TGG   AGT        774
Val   Leu   Pro   Leu   Gly   Ile   Ile   Ser   Phe   Ser   Tyr   Thr   Arg   Ile   Trp   Ser
      230                           235                           240

AAA   TTG   AAG   AAC   CAT   GTC   AGT   CCT   GGA   GCT   GCA   AAT   GAC   CAC   TAC   CAT        822
Lys   Leu   Lys   Asn   His   Val   Ser   Pro   Gly   Ala   Ala   Asn   Asp   His   Tyr   His
245                           250                           255                           260

CAG   CGA   AGG   CAA   AAA   ACC   ACC   AAA   ATG   CTG   GTG   TGT   GTG   GTG   GTG   GTG        870
Gln   Arg   Arg   Gln   Lys   Thr   Thr   Lys   Met   Leu   Val   Cys   Val   Val   Val   Val
                        265                           270                           275

TTT   GCG   GTC   AGC   TGG   CTG   CCT   CTC   CAT   GCC   TTC   CAG   CTT   GCC   GTT   GAC        918
Phe   Ala   Val   Ser   Trp   Leu   Pro   Leu   His   Ala   Phe   Gln   Leu   Ala   Val   Asp
                  280                           285                           290

ATT   GAC   AGC   CAG   GTC   CTG   GAC   CTG   AAG   GAG   TAC   AAA   CTC   ATC   TTC   ACA        966
Ile   Asp   Ser   Gln   Val   Leu   Asp   Leu   Lys   Glu   Tyr   Lys   Leu   Ile   Phe   Thr
            295                           300                           305

GTG   TTC   CAC   ATC   ATC   GCC   ATG   TGC   TCC   ACT   TTT   GCC   AAT   CCC   CTT   CTC       1014
Val   Phe   His   Ile   Ile   Ala   Met   Cys   Ser   Thr   Phe   Ala   Asn   Pro   Leu   Leu
      310                           315                           320

TAT   GGC   TGG   ATG   AAC   AGC   AAC   TAC   AGA   AAG   GCT   TTC   CTC   TCG   GCC   TTC       1062
Tyr   Gly   Trp   Met   Asn   Ser   Asn   Tyr   Arg   Lys   Ala   Phe   Leu   Ser   Ala   Phe
325                           330                           335                           340

CGC   TGT   GAG   CAG   CGG   TTG   GAT   GCC   ATT   CAC   TCT   GAG   GTG   TCC   GTG   ACA       1110
Arg   Cys   Glu   Gln   Arg   Leu   Asp   Ala   Ile   His   Ser   Glu   Val   Ser   Val   Thr
                        345                           350                           355

TTC   AAG   GCT   AAA   AAG   AAC   CTG   GAG   GTC   AGA   AAG   AAC   AGT   GGC   CCC   AAT       1158
Phe   Lys   Ala   Lys   Lys   Asn   Leu   Glu   Val   Arg   Lys   Asn   Ser   Gly   Pro   Asn
                  360                           365                           370

GAC   TCT   TTC   ACA   GAG   GCT   ACC   AAT   GTC   TAAGGAAGCT  GTGGTGTGAA                       1205
Asp   Ser   Phe   Thr   Glu   Ala   Thr   Asn   Val
            375                           380

AATGTATGGA  TGAATTCTGA  CCAGAGCTAT  GAATCTGGTT  GATGGCGGCT  CACAAGTGAA                           1265

AACTGATTTC  CCATT                                                                                1280
```

( 2 ) INFORMATION FOR SEQ ID NO:2:

( i ) SEQUENCE CHARACTERISTICS:
( A ) LENGTH: 381 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met   Gly   Pro   Ile   Gly   Ala   Glu   Ala   Asp   Glu   Asn   Gln   Thr   Val   Glu   Glu
1                       5                             10                            15
```

-continued

| | | | | | | | | | | | | | | | |
|---|---|---|---|---|---|---|---|---|---|---|---|---|---|---|---|
| Met | Lys | Val | Glu | Gln | Tyr | Gly | Pro | Gln | Thr | Thr | Pro | Arg | Gly | Glu | Leu |
| | | | 20 | | | | | 25 | | | | | 30 | | |
| Val | Pro | Asp | Pro | Glu | Pro | Glu | Leu | Ile | Asp | Ser | Thr | Lys | Leu | Ile | Glu |
| | | 35 | | | | | 40 | | | | | 45 | | | |
| Val | Gln | Val | Val | Leu | Ile | Leu | Ala | Tyr | Cys | Ser | Ile | Ile | Leu | Leu | Gly |
| | 50 | | | | | 55 | | | | | 60 | | | | |
| Val | Ile | Gly | Asn | Ser | Leu | Val | Ile | His | Val | Val | Ile | Lys | Phe | Lys | Ser |
| 65 | | | | | 70 | | | | | 75 | | | | | 80 |
| Met | Arg | Thr | Val | Thr | Asn | Phe | Phe | Ile | Ala | Asn | Leu | Ala | Val | Ala | Asp |
| | | | | 85 | | | | | 90 | | | | | 95 | |
| Leu | Leu | Val | Asn | Thr | Leu | Cys | Leu | Pro | Phe | Thr | Leu | Thr | Tyr | Thr | Leu |
| | | | 100 | | | | | 105 | | | | | 110 | | |
| Met | Gly | Glu | Trp | Lys | Met | Gly | Pro | Val | Leu | Cys | His | Leu | Val | Pro | Tyr |
| | | 115 | | | | | 120 | | | | | 125 | | | |
| Ala | Gln | Gly | Leu | Ala | Val | Gln | Val | Ser | Thr | Ile | Thr | Leu | Thr | Val | Ile |
| | 130 | | | | | 135 | | | | | 140 | | | | |
| Ala | Leu | Asp | Arg | His | Arg | Cys | Ile | Val | Tyr | His | Leu | Glu | Ser | Lys | Ile |
| 145 | | | | | 150 | | | | | 155 | | | | | 160 |
| Ser | Lys | Arg | Ile | Ser | Phe | Leu | Ile | Ile | Gly | Leu | Ala | Trp | Gly | Ile | Ser |
| | | | | 165 | | | | | 170 | | | | | 175 | |
| Ala | Leu | Leu | Ala | Ser | Pro | Leu | Ala | Ile | Phe | Arg | Glu | Tyr | Ser | Leu | Ile |
| | | | 180 | | | | | 185 | | | | | 190 | | |
| Glu | Ile | Ile | Pro | Asp | Phe | Glu | Ile | Val | Ala | Cys | Thr | Glu | Lys | Trp | Pro |
| | | 195 | | | | | 200 | | | | | 205 | | | |
| Gly | Glu | Glu | Lys | Ser | Ile | Tyr | Gly | Thr | Val | Tyr | Ser | Leu | Ser | Ser | Leu |
| | 210 | | | | | 215 | | | | | 220 | | | | |
| Leu | Ile | Leu | Tyr | Val | Leu | Pro | Leu | Gly | Ile | Ile | Ser | Phe | Ser | Tyr | Thr |
| 225 | | | | | 230 | | | | | 235 | | | | | 240 |
| Arg | Ile | Trp | Ser | Lys | Leu | Lys | Asn | His | Val | Ser | Pro | Gly | Ala | Ala | Asn |
| | | | | 245 | | | | | 250 | | | | | 255 | |
| Asp | His | Tyr | His | Gln | Arg | Arg | Gln | Lys | Thr | Thr | Lys | Met | Leu | Val | Cys |
| | | | 260 | | | | | 265 | | | | | 270 | | |
| Val | Val | Val | Val | Phe | Ala | Val | Ser | Trp | Leu | Pro | Leu | His | Ala | Phe | Gln |
| | | 275 | | | | | 280 | | | | | 285 | | | |
| Leu | Ala | Val | Asp | Ile | Asp | Ser | Gln | Val | Leu | Asp | Leu | Lys | Glu | Tyr | Lys |
| | 290 | | | | | 295 | | | | | 300 | | | | |
| Leu | Ile | Phe | Thr | Val | Phe | His | Ile | Ile | Ala | Met | Cys | Ser | Thr | Phe | Ala |
| 305 | | | | | 310 | | | | | 315 | | | | | 320 |
| Asn | Pro | Leu | Leu | Tyr | Gly | Trp | Met | Asn | Ser | Asn | Tyr | Arg | Lys | Ala | Phe |
| | | | | 325 | | | | | 330 | | | | | 335 | |
| Leu | Ser | Ala | Phe | Arg | Cys | Glu | Gln | Arg | Leu | Asp | Ala | Ile | His | Ser | Glu |
| | | | 340 | | | | | 345 | | | | | 350 | | |
| Val | Ser | Val | Thr | Phe | Lys | Ala | Lys | Lys | Asn | Leu | Glu | Val | Arg | Lys | Asn |
| | | 355 | | | | | 360 | | | | | 365 | | | |
| Ser | Gly | Pro | Asn | Asp | Ser | Phe | Thr | Glu | Ala | Thr | Asn | Val | | | |
| | 370 | | | | | 375 | | | | | 380 | | | | |